(12) United States Patent
Huck et al.

(10) Patent No.: US 8,710,044 B2
(45) Date of Patent: Apr. 29, 2014

(54) BICYCLIC AZAHETEROCYCLIC CARBOXAMIDES

(75) Inventors: Bayard R. Huck, Sudbury, MA (US); Constantin Neagu, Belmont, MA (US); Reinaldo Jones, Lowell, MA (US); Lizbeth Celeste DeSelm, Melrose, MA (US); Yufang Xiao, Lexington, MA (US); Srinivasa R. Karra, Pembroke, MA (US); Ruoxi Lan, Waltham, MA (US); Igor Mochalkin, San Diego, CA (US); Amanda E. Sutton, Hingham, MA (US); Thomas E. Richardson, Durham, NC (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/703,276

(22) PCT Filed: Jul. 1, 2011

(86) PCT No.: PCT/EP2011/003272
§ 371 (c)(1),
(2), (4) Date: Jan. 15, 2013

(87) PCT Pub. No.: WO2012/013282
PCT Pub. Date: Feb. 2, 2012

(65) Prior Publication Data
US 2013/0137677 A1    May 30, 2013

Related U.S. Application Data

(60) Provisional application No. 61/368,964, filed on Jul. 29, 2010.

(51) Int. Cl.
*A61K 31/00* (2006.01)
*A61K 31/519* (2006.01)
*C07D 239/72* (2006.01)

(52) U.S. Cl.
USPC ............... 514/210.21; 514/266.4; 544/293

(58) Field of Classification Search
None
See application file for complete search history.

(56) References Cited

FOREIGN PATENT DOCUMENTS

| WO | 03/064397 A1 | 8/2003 |
|---|---|---|
| WO | 2004/014861 A1 | 2/2004 |
| WO | 2004/092154 A1 | 10/2004 |
| WO | 2005/033086 A1 | 4/2005 |
| WO | 2005/039506 A2 | 5/2005 |
| WO | 2005/054237 A1 | 6/2005 |
| WO | 2005/056014 A1 | 6/2005 |
| WO | 2006/071819 A1 | 7/2005 |
| WO | 2005/117909 A2 | 12/2005 |
| WO | 2005/120509 A1 | 12/2005 |
| WO | 2006/120573 A2 | 11/2006 |
| WO | 2006/131835 A2 | 12/2006 |
| WO | 2006/136821 A1 | 12/2006 |
| WO | 2008/140947 A1 | 11/2008 |
| WO | 2010/093419 A1 | 8/2010 |

OTHER PUBLICATIONS

Vippagunta et al, Crystalline solids, Oct. 2000, Advanced Drug Delivery Reviews 48 (2001) 3-26.*
Hardie, G. and Hanks, S.; The Protein Kinase Facts Book. I and II, Academic Press, San Diego, CA.
Hanks, S.K., Hunter, T., FASEB J., (1995) 9:576-596.
Knighton, D.R. et al., Science, (1991) 253:407-414.
Hiles, I.D. et al. Cell, (1992) 70:419-429.
Kunz, J. et al., Cell (1993) 73:585-596.
Garcia-Bustos, J. F. et al., EMBO J. (1994) 13(10):2352-2361.
Couch, F.J. et al. Cancer Res. (1999) 59: 1408-1411.
Barlund, M. et al., Cancer Res. (2000) 60:5340-5346.
Guo-Jun, Wu et al., Cancer Res. (2000) 60, 5371-5375.

* cited by examiner

*Primary Examiner* — Jeffrey H Murray
*Assistant Examiner* — Oluwafemi Masha
(74) *Attorney, Agent, or Firm* — EMD Serono Research Institute

(57) ABSTRACT

The invention provides novel bicyclic azaheterocyclic carboxamide compounds according to Formula (I), their manufacture and use for the treatment of hyperproliferative diseases, such as cancer.

9 Claims, No Drawings

BICYCLIC AZAHETEROCYCLIC CARBOXAMIDES

FIELD OF THE INVENTION

The invention relates to a series of bicyclic azaheterocyclic carboxamide compounds that are useful in the treatment of hyperproliferative diseases, such as cancer, in mammals. Also encompassed by the present invention is the use of such compounds in the treatment of hyperproliferative diseases in mammals, especially humans, and pharmaceutical compositions containing such compounds.

SUMMARY OF THE RELATED ART

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Protein kinase 70S6K, the 70 kDa ribosomal protein kinase p70S6K (also known as SK6, p70/p85 S6 kinase, p70/p85 ribosomal S6 kinase and pp70S6K), is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. p70S6K activity is also under the control of a mTOR-containing complex (TORC1) since rapamycin acts to inhibit p70S6K activity. p70S6K is regulated by PI3K downstream targets AKT and PKC. Akt directly phosphorylates and inactivates TSC2, thereby activating mTOR. In addition, studies with mutant alleles of p70S6K that inhibited by Wortmannin but not by rapamycin suggest that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidime tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indication that p70S6K function is essential for the progression from G1 to S phase in the cell cycle. Furthermore, inhibition of cell cycle proliferation at the G1 to S phase of the cell cycle by rapamycin has been identified as a consequence of inhibition of the production of the hyperphosphorylated, activated form of p70S6K.

A role for p70S6K in tumor cell proliferation and protection of cells from apoptosis is supported based on it participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11-Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (see M. Barlund, O. Monni, J. Kononen, R. Cornelison, J. Torhorst, G. Sauter, O.-P. Kallioniemi and Kallioniemi A., Cancer Res., 2000, 60:5340-5346). It has been shown that 17q23 amplifications in breast cancer involve the PAT1, RAD51C, PS6K, and SIGMA1B genes (Cancer Res. (2000): 60, pp. 5371-5375).

The p70S6K gene has been identified as a target of amplification and overexpression in this region, and statistically significant association between amplification and poor prognosis has been observed.

Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported.

In response to energy stress, the tumor suppressor LKB1 activates AMPK which phosphorylates the TSC1/2 complex and enables it to inactivate the mTOR/p70S6K pathway. Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations.

p70S6K has been implicated in metabolic diseases and disorders. It was reported that the absence of p70S6K protects against age- and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings.

Compounds described as suitable for p70S6K inhibition are disclosed in WO 03/064397, WO 04/092154, WO 05/054237, WO 05/056014, WO 05/033086, WO 05/117909, WO 05/039506, WO 06/120573, WO 06/136821, WO 06/071819, WO 06/131835, WO 08/140,947 and PCT/US10/000,313.

DESCRIPTION OF THE INVENTION

It is the object of the present invention to provide novel p70S6K inhibitors useful in the treatment of hyperproliferative diseases, especially those related to the hyperactivity of the above mentioned protein kinases, such as cancer in mammals, with superior pharmacological properties both with respect to their activities as well as their solubility, metabolic clearance and bioavailability characteristics.

As a result, this invention provides novel, bicyclic azaheterocyclic carboxamide compounds and pharmaceutically acceptable salts, solvates or prodrugs thereof, that are kinase inhibitors and useful in the treatment of the above mentioned diseases. The compounds are defined by Formula (I):

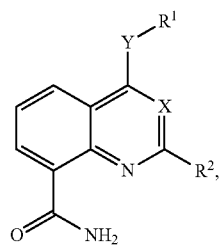

(I)

and pharmaceutically acceptable salts, solvates, solvates of salts, or prodrugs thereof, wherein:

X is N or C—$R^3$,
Y is NH, O or absent,
$R^1$ is $L^1$-$R^4$-$L^2$-$R^5$ or $L^1$-$R^4$,
$R^2$ is A, Hal, OH, OA, SH, CN, $NH_2$, $NO_2$, NHA, NH-$L^1$-Ar, NHCOA, NHCO-$L^1$-Ar, $NHSO_2$A, $NHSO_2$-$L^1$-Ar, NHCONHA, NHCONH-$L^1$-Ar, $L^1$-Ar, O-$L^1$-Ar, $L^1$-$R^4$,
$L^1$ is a single bond, methylene, or methyl substituted methylene, wherein the methylene, or the methyl group of the methyl substituted methylene may be unsubstituted or mono- or disubstituted with Hal, OH, CN, $NH_2$, NH(LA), N(LA)$_2$, $NO_2$, COOH, $N_3$, ethenyl or ethynyl, and/or monosubstituted with $R^4$, and in which one or two $CH_2$ groups may be replaced by an O or S atom or by an —NH—, —N(LA)-, —CONH—, —N(LA)COO—, —$SO_2$— or —NHCO— group,
$R^3$ is H, A, Hal, OH, COOH, SH, $NH_2$, $NO_2$ or CN,
$R^4$, $R^5$ each, independently of one another, are Ar, or cyclic A which may be mono- or disubstituted by Hal or LA,
$L^2$ is —NHCO—, —NHCOO—, —NHCONH—, —NH-CONA-, —NHCOA-, —O—, —S—, —NH—, —$NHSO_2$—, —$SO_2$NH—, —CONH—, —CONH-CONH—, —NHCONHCO—, or -A-,
Ar is a mono- or bicyclic aromatic homo- or heterocycle having 0, 1, 2, 3 or 4 N, O and/or S atoms and 5, 6, 7, 8, 9, or 10 skeleton atoms, which may be unsubstituted or, independently of one another, mono-, di- or trisubstituted by Hal, A, OH, SH, OA, $NH_2$, NHA, $NA_2$, $NO_2$, CN, OCN, SCN, COOH, COOA, $CONH_2$, CONHA, $CONA_2$,
NHCOA, NHCONHA, $NHCONH_2$, $NHSO_2$A, CHO, COA, $SO_2NH_2$, $SO_2$A and/or $SO_2$Hal, and in which a ring N-atom may be substituted by an O-atom to form an N—oxide group,
and in which in the case of a bicyclic aromatic cycle on of the two rings may be partly saturated,
A is unbranched or branched linear or cyclic alkyl having 1, 2, 3, 4, 5, 6, 7 or 8 C atoms, in which one or two $CH_2$ groups may be replaced by an O or S atom and/or by an —NH—, —CO—, —NHCOO—, —NHCONH—, —N(LA)-, —CONH—, —NHCO— or —CH=CH— group, and in which 1-3 H atoms may be replaced by Hal, and in which one or two $CH_3$ groups may be replaced by OH, SH, $NH_2$, NH(LA), N(LA)$_2$, NHCOOH, $NHCONH_2$ or CN,
LA is unbranched or branched, linear alkyl having 1, 2, 3 or 4 C atoms, wherein 1, 2 or 3 H atoms may be replaced by Hal,
Hal is F, Cl, Br or I.

In general, all residues which occur more than once may be identical or different, i.e. are independent of one another. Above and below, the residues and parameters have the meanings indicated for the Formula (I), unless expressly indicated otherwise.

Accordingly, the invention relates, in particular, to the compounds of the Formula (I) in which at least one of the said residues has one of the preferred meanings indicated below.

Hal denotes fluorine, chlorine, bromine or iodine, in particular fluorine or chlorine.

"A" denotes, for example, methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

"A" further denotes alkyl as defined above, in which one or two $CH_2$ groups may be replaced by O or S atoms and/or by NH, N(LA), CONH, NHCO or —CH=CH-groups and/or in addition 1-3 H atoms may be replaced by F and/or Cl, such as, for example, trifluoromethyl, pentafluoroethyl, 1,1-difluoromethyl, 1,1,1-trifluoroethyl, methoxy, ethoxy, n-propoxy, isopropoxy, n-butoxy, isobutoxy, sec-butoxy or tert-butoxy.

In other examples of "A", one or two $CH_3$ groups is replaced by OH, SH, $NH_2$, N(LA)H, N(LA)$_2$ or CN, such as, for example, N,N'-dimethylaminoalkyl, 2-aminoethyl, 3-aminopropyl, 4-aminobutyl, 5-aminopentyl, 3-aminomethylcyclobutyl or cyanoalkyl. Cyclic A preferably denotes cyclopropyl, cyclobutyl, cyclopentyl, cyclohexyl or cycloheptyl.

"LA" denotes unbranched or branched, linear alkyl having 1, 2, 3 or 4 C atoms, wherein 1, 2 or 3 H atoms may be replaced by Hal, e.g. methyl, ethyl, trifluoromethyl, difluoromethyl, 1,1,1-trifluoroethyl, propyl, isopropyl, butyl, isobutyl, sec-butyl or tert-butyl.

"Ar" denotes, for example, unsubstituted phenyl, naphthyl or biphenyl, furthermore preferably, for example, phenyl, naphthyl or biphenyl, each of which is mono-, di- or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl.

"Ar" furthermore denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl, (4-methoxyphenyl)methyl, (3-methoxyphenyl)methyl, (4-methoxyphenyl)ethyl, (3-methoxyphenyl)ethyl.

"Ar" furthermore preferably denotes 2-, 3- or 4-phenyl, 2-, 3- or 4-phenylmethyl, 2-, 3- or 4-phenylethyl, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 3- or 4-pyridylmethyl, 2-, 3- or 4-pyridylethyl, 2-, 4-, 5- or 6-pyrimidinyl, 2-, 3-, 5-, or 6-pyrazin-1- or 4-yl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-oxadiazol-2-yl, 1,3,4-thiadiazol-2- or -5-yl, 1,2,4-thiadiazol-3- or -5-yl, 1,2,3-thiadiazol-4- or -5-yl, 3- or 4-pyridazinyl, 1-, 2-, 3-, 4-, 5-, 6- or 7-indolyl, 2-, 3-, 4- or 5-isoindolyl, 2-, 6, - or 8-purinyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 3-, 4-, 5-, 6-, 7- or 8-isoquinolinyl, 3-, 4-, 5-, 6-, 7- or 8-quinolinyl, 2-, 4-, 5-, 6-, 7- or 8-quinazolinyl, quinoxalin-2-, 3-, 4- or 5-yl, 4-, 5-, or 6-phthalazinyl, 2-, 3-, 5-, 6-, 7- or 8-2H-benzo-1,4-oxazinyl, further preferably 1,3-benzodioxol-2-, 4- or 5-yl, thiophen-2- or 3-yl, 1,4-benzodioxan-6-yl, 2,1,3-benzothiadiazol-4- or -5-yl or 2,1,3-benzoxadiazol-5-yl, furan-2- or 3-yl, 2,3-dihydro-benzofuran-2-, 3-, 4- or 5-yl, each of which is unsubstituted or may be mono-, di- or trisubstituted, for example, by carbonyl oxygen, F, Cl, Br, methyl, ethyl, propyl, phenyl, benzyl, —CH$_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl and/or methylsulfonyl.

In those cases where $R^1$ is $L^1$-$R^4$-$L^2$-$R^5$, residue $R^4$ obviously has a bridging function, and is substituted by linkers $L^1$ and $L^2$, independently of any further substitutions it may have.

The term "substituted" preferably relates to the substitution by the above-mentioned substituents, where a plurality of different degrees of substitution are possible, unless indicated otherwise.

All physiologically acceptable salts, derivatives, solvates, solvates of salts, and stereoisomers of these compounds, including mixtures thereof in all ratios, are also in accordance with the invention.

The compounds of the Formula (I) may have one or more centres of chirality. They may accordingly occur in various enantiomeric forms and be in racemic or optically active form. The invention therefore also relates to the optically active forms (stereoisomers), the enantiomers, the racemates, the diastereomers and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

In a preferred group of compounds of Formula (I) the variables and substituents have the following meanings:
X is N,
Y is NH,
$R^1$ is $L^1$-$R^4$,
$R^2$ is LA, Hal, OH, O(LA), SH, CN, NH$_2$, NO$_2$, NH(LA), NHCO(LA), NHSO$_2$(LA), NHCONH(LA),
$L^1$ is methyl substituted methylene, wherein the methyl group of the methyl substituted methylene is monosubstituted with NH$_2$ or NH(LA), N(LA)$_2$, or cyclic A which may be mono- or disubstituted by Hal or LA,
$R^4$ is a monocyclic aromatic homo- or heterocycle having 0, 1 or 2 N, O and/or S atoms and 5 or 6 skeleton atoms, which may be unsubstituted or, independently of one another, mono-, di- or trisubstituted by Hal, A, OH, SH, OA, NH$_2$, NHA, NA$_2$, NO$_2$, CN, OCN, SCN, COOH, COOA, CONH$_2$, CONHA, CONA$_2$, NHCOA, NHCONHA, NHCONH$_2$, NHSO$_2$A, CHO, COA, SO$_2$NH$_2$, SO$_2$A and/or SO$_2$Hal,
A is unbranched or branched linear or cyclic alkyl having 1, 2, 3, 4, 5, 6, 7 or 8 C atoms, in which one or two CH$_2$ groups may be replaced by an O or S atom and/or by an —NH—, —CO—, —NHCOO—, —NHCONH—. —N(LA)-, —CONH—, —NHCO— or —CH=CH— group, and in which 1-3 H atoms may be replaced by Hal, and in which one or two CH$_3$ groups may be replaced by OH, SH, NH$_2$, NH(LA), N(LA)$_2$, NHCOOH, NHCONH$_2$ or CN, LA is unbranched or branched, linear alkyl having 1, 2, 3 or 4 C atoms, wherein 1, 2 or 3 H atoms may be replaced by Hal,
Hal is F, Cl, Br or I.

Further preferred are compounds of Subformulae 1 to 19 of Formulae (I), in which the residues not designated in greater detail have the meaning indicated for the preferred group of compounds above, and pharmaceutically acceptable salts, solvates, solvates of salts, or prodrugs thereof, wherein
in Subformula 1
$R^2$ is LA,
in Subformula 2
$L^1$ is methyl substituted methylene, wherein the methyl group of the methyl substituted methylene is monosubstituted with methylamino, dimethylamino or azetidine,
in Subformula 3
$R^4$ is phenyl which is unsubstituted or monosubstituted with Hal,
in Subformula 4
$R^2$ is methyl, ethyl, isopropyl or trifluoromethyl,
in Subformula 5
$L^1$ is methyl substituted methylene, wherein the methyl group of the methyl substituted methylene is monosubstituted with methylamino,
in Subformula 6
$L^1$ is methyl substituted methylene, wherein the methyl group of the methyl substituted methylene is monosubstituted with azetidin-1-yl,
in Subformula 7
$R^4$ is phenyl which is unsubstituted,
in Subformula 8
$R^4$ is phenyl which is meta or para substituted with F or Cl,
in Subformula 9
$R^2$ is LA,
$L^1$ is methyl substituted methylene, wherein the methyl group of the methyl substituted methylene is monosubstituted with methylamino or azetidine,
in Subformula 10
$R^2$ is LA,
$R^4$ is phenyl which is unsubstituted or monosubstituted with Hal,
in Subformula 11
$L^1$ is methyl substituted methylene, wherein the methyl group of the methyl substituted methylene is monosubstituted with methylamino or azetidine,
$R^4$ is phenyl which is unsubstituted or monosubstituted with Hal,
in Subformula 12
$R^2$ is LA,
$L^1$ is methyl substituted methylene, wherein the methyl group of the methyl substituted methylene is monosubstituted with methylamino or azetidine,
$R^4$ is phenyl which is unsubstituted or monosubstituted with Hal,
in Subformula 13
$R^2$ is methyl, ethyl, isopropyl or trifluoromethyl,
$L^1$ is methyl substituted methylene, wherein the methyl group of the methyl substituted methylene is monosubstituted with methylamino or azetidine,
$R^4$ is phenyl which is unsubstituted or monosubstituted with Hal,
in Subformula 14
$R^2$ is LA,
$L^1$ is methyl substituted methylene, wherein the methyl group of the methyl substituted methylene is monosubstituted with methylamino or azetidine,
$R^4$ is phenyl which is meta or para substituted with F or Cl,
in Subformula 15
$R^2$ is methyl, ethyl, isopropyl or trifluoromethyl,
$L^1$ is methyl substituted methylene, wherein the methyl group of the methyl substituted methylene is monosubstituted with methylamino or azetidine,
$R^4$ is phenyl which is meta or para substituted with F or Cl,
in Subformula 16
$R^2$ is methyl, ethyl, isopropyl or trifluoromethyl,
$L^1$ is methyl substituted methylene, wherein the methyl group of the methyl substituted methylene is monosubstituted with methylamino,
$R^4$ is phenyl which is meta or para substituted with F or Cl,
in Subformula 17
$R^2$ is methyl, ethyl, isopropyl or trifluoromethyl,
$L^1$ is methyl substituted methylene, wherein the methyl group of the methyl substituted methylene is monosubstituted with azetidin-1-yl,
$R^4$ is phenyl which is meta or para substituted with F or Cl,
in Subformula 18
$R^2$ is methyl, ethyl, isopropyl or trifluoromethyl,
$L^1$ is methyl substituted methylene, wherein the methyl group of the methyl substituted methylene is monosubstituted with methylamino or azetidine,
$R^4$ is phenyl which is meta substituted with F or Cl,
in Subformula 19
$R^2$ is methyl, ethyl, isopropyl or trifluoromethyl,
$L^1$ is methyl substituted methylene, wherein the methyl group of the methyl substituted methylene is monosubstituted with methylamino or azetidin-1-yl,
$R^4$ is phenyl which is meta substituted with F or Cl,
and the remaining residues have the meaning as indicated for Formula (I) above.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt or a solvate, or a solvate of such salt. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

"Solvates" means solvent additions forms that contain either stoichiometric or non stoichiometric amounts of solvent. Many compounds have a tendency to trap a fixed molar ratio of solvent molecules in the crystalline solid state, thus forming a solvate. For example, if the solvent is water the solvate formed is a hydrate, when the solvent is alcohol, the solvate formed is an alcoholate, if the solvent is an ether, the solvate formed is an etherate. Specific examples of solvates include mono- or dihydrates, methanolates, ethanolates or diethyletherates.

Those skilled in the art appreciate that in many cases the solvates of pharmaceutical active ingredients, or their pharmaceutically acceptable salts, are used in pharmaceutical compositions, and know how to obtain such solvates.

Furthermore, the present invention relates to pharmaceutical compositions comprising a compound of the present invention, or a prodrug compound thereof, or a pharmaceutically acceptable salt or solvate thereof as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other p70S6K inhibitors. The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. Preferably, the cancer to be treated is chosen from breast, colorectal, lung, prostate or pancreatic cancer or glioblastoma.

The invention also relates to the use of compounds according to the invention for the preparation of a medicament for the treatment of hyperproliferative diseases related to the hyperactivity of p70S6K as well as diseases modulated by the p70S6K cascade in mammals, or disorders mediated by aberrant proliferation, such as cancer and inflammation.

The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or solvate thereof, and a pharmaceutically acceptable carrier.

In one embodiment, said compound or pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and sclerodema, diabetes, diabetic retinopathy, retinopathy of prematurity and age-related macular degeneration.

This invention also relates to a compound or pharmaceutical composition for inhibiting abnormal cell growth in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of another protein kinase, such as Akt, Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for inhibiting abnormal cell growth in a mammal or treating a hyperproliferative disorder that comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein. The invention also relates to a method for inhibiting abnormal cell growth in a mammal that comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of a) an effective amount of a compound according to the invention or a physiologically acceptable salt, solvate or prodrug thereof, and b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Experimental Section

Some abbreviations that may appear in this application are as follows:

Abbreviations

| Designation | |
|---|---|
| ACN | Acetonitrile |
| ATP | Adenosine triphosphate |
| b | Broad peak |
| d | Doublet |
| DMSO | Dimethylsulfoxide |
| DIEA | N,N-Diisopropylethylamine |
| DTT | Dithiothreitol |
| EDTA | Ethylenediaminetetraacetic acid |
| equiv. | Equivalents |
| Et | Ethyl |
| h | Hour |
| HEPES | 4-(2-hydroxyethyl)-1-piperazineethanesulfonic acid |
| HPLC | High pressure liquid chromatography |
| LC/MS | Liquid chromatography coupled to mass spectrometry |
| m | Multiplet |
| M | Molecular ion |
| m/z | Mass-to-charge ratio |
| Me | Methyl |
| min | Minute |
| MS | Mass spectrometry |
| N | Normal (unit of concentration) |
| NMO | 4-methylmorpholine N-oxide |
| NMR | Nuclear Magnetic Resonance |
| PG | Protecting group |
| psi | Pounds per square inch |
| q | Quartette (or quartet) |
| Rf | Retention factor |
| RT | Room temperature |
| Rt. | Retention time |
| s | Singlet |
| Tert | Tertiary |
| TEA | Triethylamine |
| TFA | Trifluoroacetic acid |
| THAB | Tetrahexylammonium bromide |
| THF | Tetrahydrofuran |
| UV | ultraviolet |
| VIS | visible |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following schemes and examples. Unless otherwise indicated in the schemes, the variables have the same meaning as described above. Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

The present invention also relates to processes for manufacturing the compounds of Formula (I) and Subformulae 1-19 according to the hereinafter described schemes and working examples.

In particular, the present invention relates to a process for the manufacture of compounds of Formula (I), wherein X is N and Y is NH, and all other substituents have the meaning as defined for Formula (I) in claim 1, wherein a carboxylic acid ester of Formula (IV)

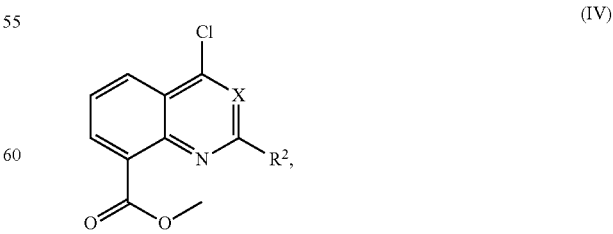

(IV)

is reacted with a compound of Formula (III)

(III), to yield a compound of Formula (II)

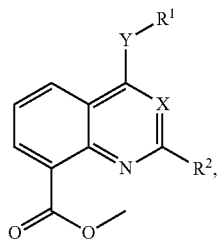
(II)

which is finally converted into the carboxylic amide of Formula (I)

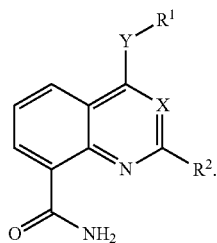
(I)

General Synthetic Procedures

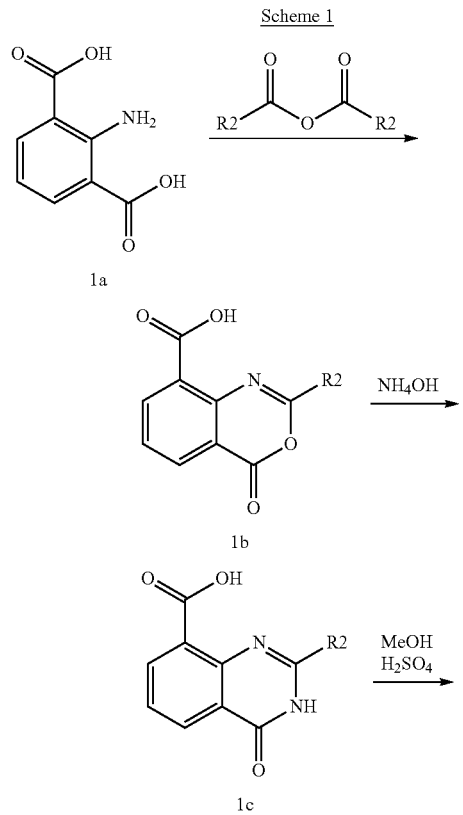

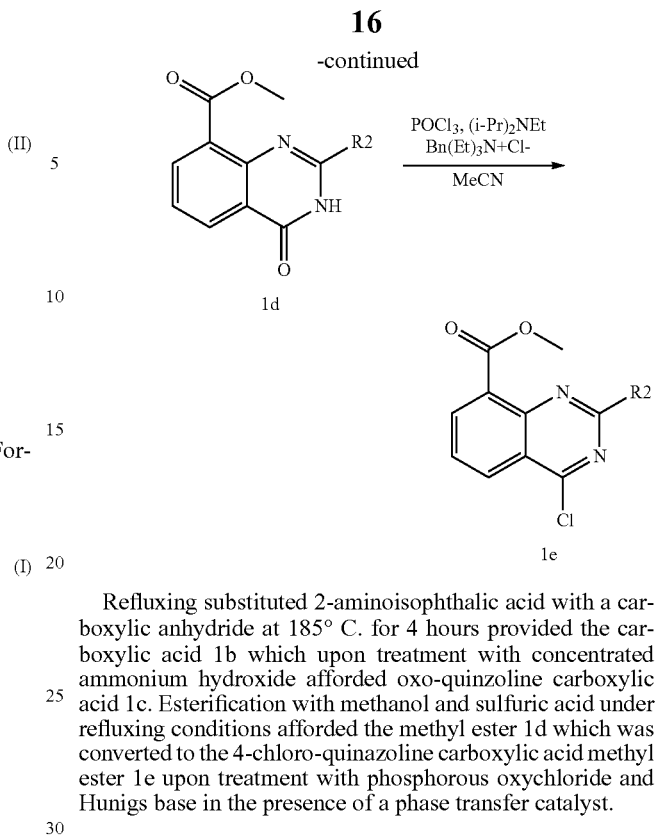

Refluxing substituted 2-aminoisophthalic acid with a carboxylic anhydride at 185° C. for 4 hours provided the carboxylic acid 1b which upon treatment with concentrated ammonium hydroxide afforded oxo-quinzoline carboxylic acid 1c. Esterification with methanol and sulfuric acid under refluxing conditions afforded the methyl ester 1d which was converted to the 4-chloro-quinazoline carboxylic acid methyl ester 1e upon treatment with phosphorous oxychloride and Hunigs base in the presence of a phase transfer catalyst.

Scheme 2

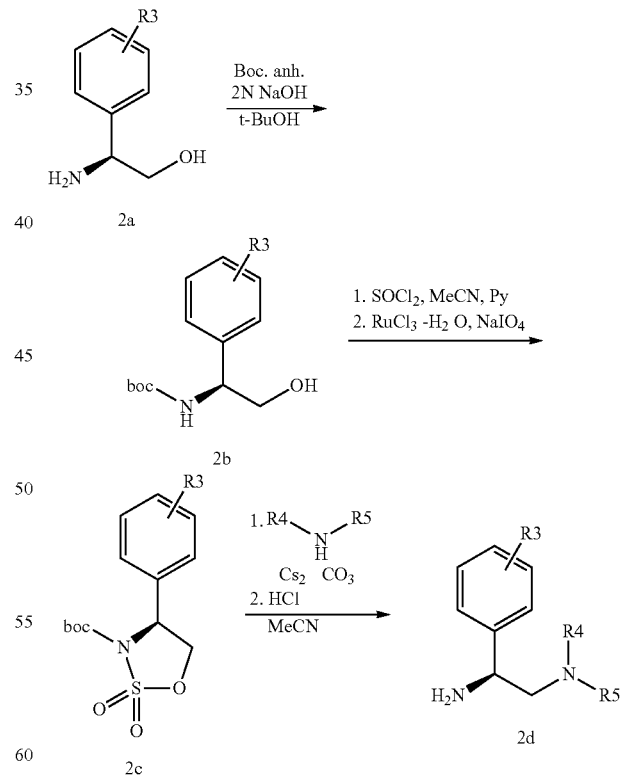

Amino-alcohol 2a was treated with di-tertbutyl dicarbonate in the presence of 2N sodium hydroxide and t-butanol as solvent to afford the Boc-protected amino alcohol 2b. Cyclization with thionyl chloride to the sulfoxide intermediate was followed by in oxidation with sodium periodate in the presence of ruthenium catalyst to provide the cyclic intermediate 2c. Nucleophilic attack of 2c with a secondary amine and in-situ Boc deprotection with hydrochloric acid/methanol afforded the desired amine 2d.

Scheme 3

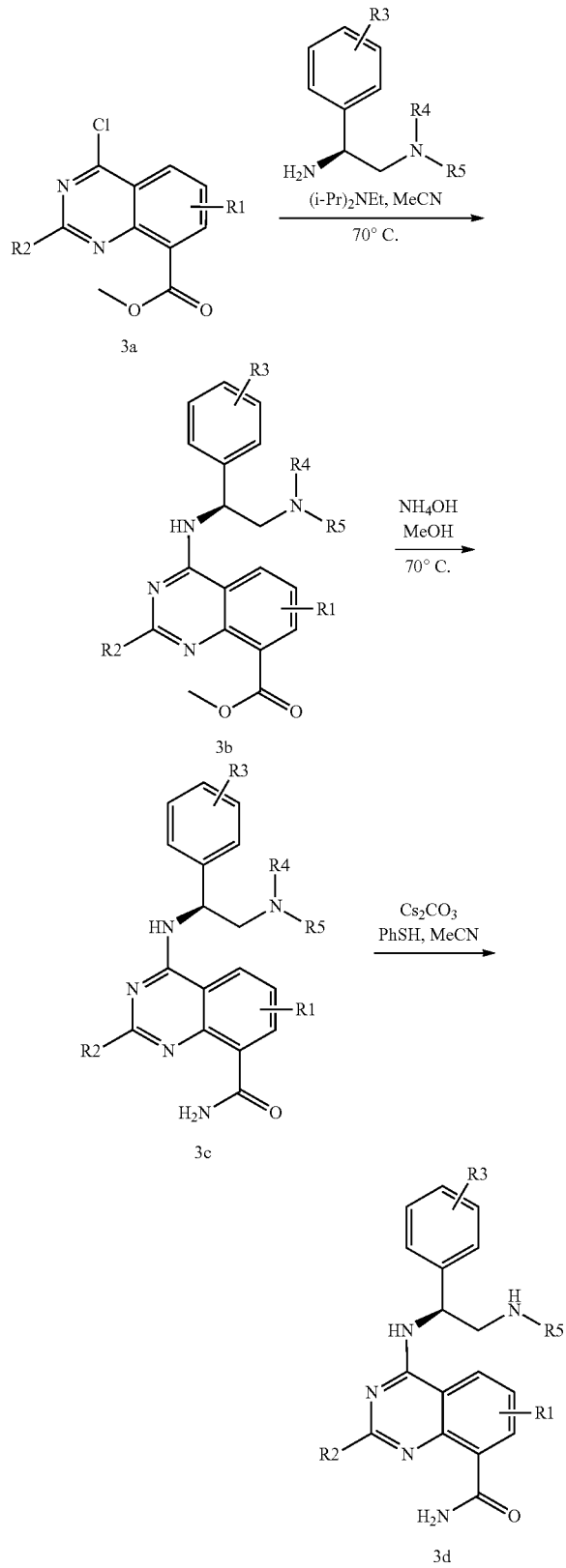

4-Chloro quinazoline derivative 3a was reacted with the primary amine 2d in the presence of Hunig's base to provide the 4-amino quinazoline intermediate 3b. Ammonolysis of the ester group with 7N ammonia/methanol solution afforded carboxamide 3c. When R4 is a protecting Nosyl group, deprotection with cesium carbonate in the presence of thiophenol provides 3d.

Analytical Methodology

Analytical LC/MS was performed using the following three methods:

Method A: A Discovery $C^{18}$, 5 μm, 3×30 mm column was used at a flow rate of 400 μL/min, sample loop 5 μL, mobile phase: (A) water with 0.1% formic acid, mobile phase, (B) methanol with 0.1% formic acid; retention times are given in minutes. Method details: (I) runs on a Quaternary Pump G1311A (Agilent) with UV/VIS diode array detector G1315B (Agilent) and Finnigan LCQ Duo MS detector in ESI+modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B: A Waters Symmetry $C^{18}$, 3.5 μm, 4.6×75 mm column at a flow rate of 1 mL/min, sample loop 10 μL, mobile phase (A) is water with 0.05% TFA, mobile phase (B) is ACN with 0.05% TFA; retention times are given in minutes. Methods details: (I) runs on a Binary Pump G1312A (Agilent) with UV/Vis diode array detector G1315B (Agilent) and Agilent G1956B (SL) MS detector in ESI+mode with UV-detection at 254 and 280 nm with a gradient of 20-85% (B) in a 10 min linear gradient (II) hold for 1 min at 85% (B) (III) decrease from 20-85% (B) in a 0.2 min linear gradient (IV) hold for 3.8 min at 20% (B).

Method C: Gradient: 4.2 min/Flow: 2 ml/min 99:01–0:100 Water+0.1% (Vol.) TFA; Acetonitril+0.1% (Vol.) TFA; 0.0 to 0.2 min: 99:01; 0.2 to 3.8 min: 99:01→0:100; 3.8 to 4.2 min: 0:100; Column: Chromolith Performance RP18e; 100 mm long, 3 mm diameter; Wavelength: 220 nm.

Analytical Chiral HPLC

Analytical chiral HPLC was performed using a ChiralPak AD-H column (250×4.6 mm) from Daicel Chemical Industries, Ltd. on an Agilent 1100 Series system. The method used a 5.0 μL injection volume, with a flow rate of 1 mL/min of 100% methanol for 15 min at 25° C., and UV-detection at 254 and 280 nm.

Preparative HPLC

Preparative HPLC was performed using either a Waters Atlantis $dC_{18}$ OBD™ 10 μM (30×250 mm) column or a Waters Sunfire Prep $O_{18}$ OBD 10 μM (30×250 mm) column. The columns were used at a flow rate of 60 mL/min on a Waters Prep LC 4000 System equipped with a sample loop (10 mL) and an ISCO UA-6 UV/Vis detector. The mobile phase was drawn from two solvent reservoirs containing (A) water and (B) HPLC-grade acetonitrile. A typical preparative run used a linear gradient (e.g., 0-60% solvent B over 60 min).

EXAMPLES

The working examples presented below are intended to illustrate particular embodiments of the invention, and are not intended to limit the scope of the specification or the claims in any way.

Chemical Synthesis

In this section experimental details are provided for a number of Example compounds according to Formula (I), and synthesis intermediates thereof.

Synthesis Intermediates

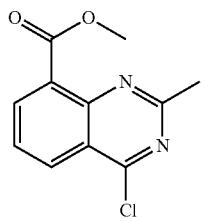 [SMILES: COC(=O)c1cccc2c(Cl)nc(C)nc12]

Methyl 4-chloro-2-methylquinazoline-8-carboxylate
(1)

2-methyl-4-oxo-4H-3,1-benzoxazine-8-carboxylic acid

2-Aminoisophthalic acid (50.0 g; 276.0 mmol) and $Ac_2O$ (250.0 ml; 5.00 V) were combined and heated to 140° C. for 4 h. The reaction mixture was cooled to room temperature and distilled under high vacuum on the rotary evaporator. The remaining AcOH was removed by azeotropic distillation with toluene. The residue was slurried with ethyl ether, filtered, and the solid was dried under vacuum to provide the desired intermediate (50.3 g, 89% yield).

2-Methyl-4-oxo-3,4-dihydroquinazoline-8-carboxylic acid

2-Methyl-4-oxo-4H-3,1-benzoxazine-8-carboxylic acid (51.5 g; 251.26 mmol) was dissolved in $NH_4OH$ (360.0 ml; 6.98 V; 28% solution). Ammonium acetate (77.5 g; 1.005 mmol) was added, and the reaction mixture was heated at 80° C. for 2 h. The reaction mixture was cooled to room temperature and diluted with MeOH (40 mL) then heated for 72 h at 80° C. in a pressure bottle. The reaction mixture was concentrated on the rotary evaporator then cooled on ice and filtered. The solid was dried under vacuum to provide the desired product (33.5 g, 65% yield).

Methyl 2-methyl-4-oxo-3,4-dihydroquinazoline-8-carboxylate

2-Methyl-4-oxo-3,4-dihydroquinazoline-8-carboxylic acid (28.2 g; 138.11 mmol) was dissolved in dry MeOH (1000 mL). Sulfuric acid (29.4 ml; 552.44 mmol) was added dropwise to the reaction mixture under argon. The reaction mixture was refluxed overnight, cooled to room temperature, and then concentrated. The solid was filtered and dried under vacuum to provide the desired intermediate as a sulfate salt. The sulfate salt (40.6 g, 128.36 mmol) was treated with $K_2CO_3$ (8.87 g, 64.18 mmol) in $H_2O$ (100 mL). Upon dissolution, an off-white precipitate was formed. Additional $H_2O$ (100 mL) was added, and the pH was adjusted between 6 and 7. The off-white solid was filtered, washed with $H_2O$ (150 mL), and dried under vacuum to provide the desired intermediate (17.90 g, 64% yield). The aqueous layer was extracted with EtOAc (250 mL) to provide another 1.10 g (4% yield).

Methyl 4-chloro-2-methylquinazoline-8-carboxylate

A suspension of methyl 2-methyl-4-oxo-3,4-dihydroquinazoline-8-carboxylate (2.00 g; 9.17 mmol; 1.00 eq.) and benzyltriethylammonium chloride (4.18 g, 18.33 mmol) in dry $CH_3CN$ (5 mL) was treated with DIEA (1.75 mL, 10.1 mmol) and stirred as $POCl_3$ (7.3 mL, 80.2 mmol) was slowly added to the flask. The contents were warmed to 90° C. for 30 min, cooled to ~50° C., and slowly poured into a 2N NaOH (80 mL, 160 mmol) and water (80 mL) that was cooling in an acetone/dry-ice bath (ice formed in the flask). The off-red solid that precipitated was filtered, washed with 10% aqueous $K_2CO_3$ (15 mL), and dried under vacuum to afford 1 (1.35 g; 62% yield). LC-MS [236.8 (M+1)]

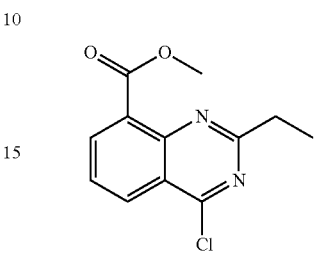

Methyl 4-chloro-2-ethylquinazoline-8-carboxylate
(2)

This compound was prepared following the general procedure of example 1 using propionic anhydride. LC-MS [251.0 (M+1)]

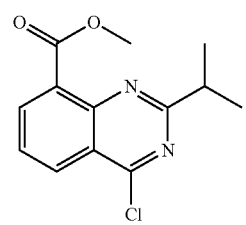 [SMILES: COC(=O)c1cccc2c(Cl)nc(C(C)C)nc12]

Methyl 4-chloro-2-isopropylquinazoline-8-carboxylate (3)

This compound was prepared following the general procedure of example 1 using isobutyric anhydride. LC-MS [265.0 (M+1)]

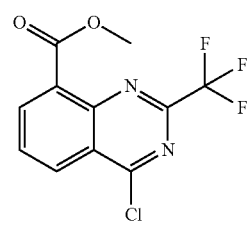 [SMILES: COC(=O)c1cccc2c(Cl)nc(C(F)(F)F)nc12]

4-Chloro-2-trifluoromethyl-quinazoline-8-carboxylic acid methyl ester (4)

This compound was prepared following the general procedure of example 1 using trifluoroacetic anhydride. LC-MS [291.0 (M+1)]

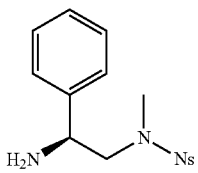

N-[(2S)-2-amino-2-phenylethyl]-N-methyl-4-nitrobenzenesulfonamide (5)

tert-Butyl [(1S)-phenyl)-2-hydroxyethyl]carbamate

S-Amino alcohol (1 g), di-tert-butyl dicarbonate, and NaOH were suspended in tBuOH, and stirred for 5 h at 70 C. The reaction mixture was cooled to 50 C, added to $H_2O$ (50 mL), and stirred vigorously at RT for 1 h. The resulting white precipitate was filtered, washed with $H_2O$, and dried under vacuum to provide the desired intermediate.

tert-Butyl [(1S)-phenyl)-2-hydroxyethyl]carbamate

A solution of $SOCl_2$ in MeCN (12.0 ml) under $N_2$ atm was cooled to −40° C. A solution of tert-butyl [(1S)-phenyl)-2-hydroxyethyl]carbamate in $CH_3CN$ (12.0 ml) was added slowly dropwise via syringe. Pyridine was added dropwise and the reaction was allowed to stir for 30 min before removing the dry ice/MeCN bath.

The reaction mixture was stirred for 2 h, and then concentrated. The residue was dissolved in EtOAc and filtered through a silica plug. The filtrate was concentrated and dried under vacuum. The resulting intermediate, trichloro-ruthenium hydrate (0.08 g; 0.35 mmol), and sodium metaperiodate (0.21 ml; 4.16 mmol) were dissolved in $CH_3CN$ (3 mL) and $H_2O$ (3 mL), and stirred overnight at room temperature. The reaction was diluted with $H_2O$ and extracted with EtOAc (3×). The combined organic layers were washed with brine, dried over $MgSO_4$, filtered and concentrated. The crude product was purified via Biotage eluting with a gradient of 0 to 30% EtOAc in hexanes to afford the desired intermediate (600 mg, 45% overall yield).

tert-Butyl ((1S)-2-{methyl[(4-nitrophenyl)sulfonyl]amino}-1-phenylethyl)carbamate tert-Butyl (4S)-4-phenyl-1,2,3-oxathiazolidine-3-carboxylate 2,2-dioxide (1 g; 3.34 mmol), N-methyl-4-nitrobenzenesulfonamide (722 mg; 3.34 mmol), and $Cs_2CO_3$ (0.40 ml; 5.01 mmol) were dissolved in $CH_3CN$ (25 ml), and stirred overnight. The reaction mixture was filtered, washed with $H_2O$ (50 ml), and dried under vacuum to provide the desired intermediate (1.12 g; 77%).

N-[(2S)-2-amino-2-phenylethyl]-N-methyl-4-nitrobenzenesulfonamide

4 M HCl/dioxane (6 ml) was added to tert-butyl ((1S)-2-{methyl[(4-nitrophenyl) sulfonyl]amino}-1-phenylethyl) carbamate (1.05 g; 2.41 mmol) and stirred at 50° C. for 2 hours. The reaction mixture was evaporated under vacuum to provide 5 (763 mg; 85% yield) as a white solid (HCl salt). LC-MS [336 (M+1)]

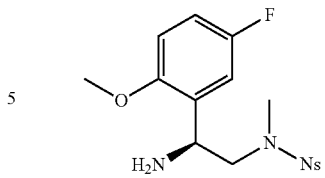

N-[(2S)-2-amino-2-(5-fluoro-2-methoxyphenyl)ethyl]-N-methyl-4-nitrobenzenesulfonamide (6)

This compound was prepared following the general procedure of example 5 using N-methyl-4-nitrobenzenesulfonamide and the corresponding amino alcohol. LC-MS [384 (M+1)]

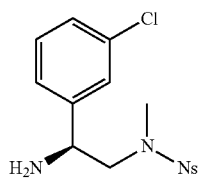

N-[(2S)-2-amino-2-(3-chlorophenyl)ethyl]-N-methyl-4-nitrobenzenesulfonamide (7)

This compound was prepared following the general procedure of example 5 using N-methyl-4-nitrobenzenesulfonamide and the corresponding amino alcohol. LC-MS [407 (M+1)]

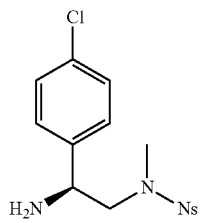

N-[(2S)-2-amino-2-(4-chlorophenyl)ethyl]-N-methyl-4-nitrobenzenesulfonamide (8)

This compound was prepared following the general procedure of example 5 using N-methyl-4-nitrobenzenesulfonamide and the corresponding amino alcohol. LC-MS [370 (M+1)]

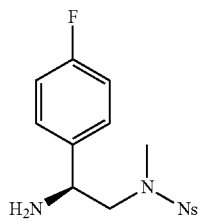

N-[(2S)-2-amino-2-(4-fluorophenyl)ethyl]-N-methyl-4-nitrobenzenesulfonamide (9)

This compound was prepared following the general procedure of example 5 using N-methyl-4-nitrobenzenesulfonamide and the corresponding amino alcohol. LC-MS [354 (M+1)]

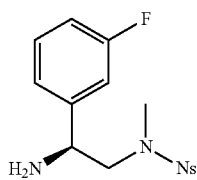

N-[(2S)-2-amino-2-(3-fluorophenyl)ethyl]-N-methyl-4-nitrobenzenesulfonamide (10)

This compound was prepared following the general procedure of example 5 using N-methyl-4-nitrobenzenesulfonamide and the corresponding amino alcohol. LC-MS [354 (M+1)]

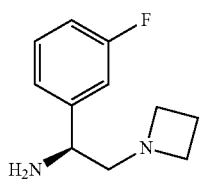

(1S)-2-azetidin-1-yl-1-(3-fluorophenyl)ethanamine (11)

This compound was prepared following the general procedure of example 5 using azetidine and the corresponding amino alcohol. LC-MS [195 (M+1)]

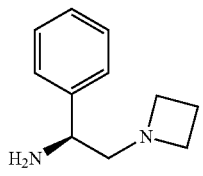

(S)-2-Azetidin-1-yl-1-phenyl-ethylamine (12)

This compound was prepared following the general procedure of example 5 using azetidine and the corresponding amino alcohol. LC-MS [177 (M+1)]

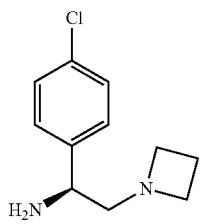 [SMILES: N[C@H](CN1CCC1)c1ccc(Cl)cc1]

(S)-2-Azetidin-1-yl-1-(4-chloro-phenyl)-ethylamine (13)

This compound was prepared following the general procedure of example 5 using azetidine and the corresponding amino alcohol. LC-MS [211 (M+1)]

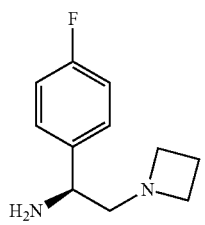 [SMILES: N[C@H](CN1CCC1)c1ccc(F)cc1]

(1S)-2-azetidin-1-yl-1-(4-fluorophenyl)ethanamine (14)

This compound was prepared following the general procedure of example 5 using azetidine and the corresponding amino alcohol. LC-MS [195 (M+1)]

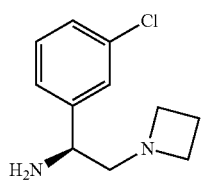 [SMILES: N[C@H](CN1CCC1)c1cccc(Cl)c1]

(S)-2-Azetidin-1-yl-1-(3-chloro-phenyl)-ethylamine (15)

This compound was prepared following the general procedure of example 5 using azetidine and the corresponding amino alcohol. LC-MS [211 (M+1)]

Example Compounds According to Formula (I)

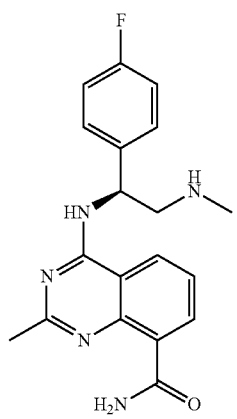

4-{[(1S)-1-(4-fluorophenyl)-2-(methylamino)ethyl]amino}-2-methylquinazoline-8-carboxamide (16)

IC$_{50}$ p70S6K [nM]: 2.8

Methyl 4-[((1S)-1-(4-fluorophenyl)-2-{methyl[(4-nitrophenyl)sulfonyl]amino}ethyl)-amino]-2-methylquinazoline-8-carboxylate 1 (100 mg; 0.42 mmol), 9 (123 mg; 0.32 mmol), and DIEA (0.23 mL) were dissolved in CH$_3$CN (4 ml), and stirred at 70° C. for 72 h. The reaction mixture was concentrated to provide the desired crude intermediate.

4-[((1S)-1-(4-Fluorophenyl)-2-{methyl[(4-nitrophenyl)sulfonyl]amino}ethyl)amino]-2-methylquinazoline-8-carboxamide Crude methyl 4-[((1S)-1-(4-fluorophenyl)-2-{methyl[(4-nitrophenyl)sulfonyl]-amino}ethyl)amino]-2-methylquinazoline-8-carboxylate (177 mg; 0.32 mmol) was treated with methanolic ammonia (10 ml, 7M), and stirred at 70° C. overnight. The reaction mixture was concentrated to provide the desired crude intermediate. (M+H) 539.1

4-{[(1S)-1-(4-Fluorophenyl)-2-(methylamino)ethyl]amino}-2-methylquinazoline-8-carboxamide Crude 4-[((1S)-1-(4-Fluorophenyl)-2-{methyl[(4-nitrophenyl)sulfonyl]amino}ethyl)-amino]-2-methylquinazoline-8-carboxamide (161 mg; 0.30 mmol) and Cs$_2$CO$_3$ (488 mg; 1.50 mmol) were suspended in CH$_3$CN (7 ml), and stirred for 10 minutes at room temperature. Benzenethiol (0.12 ml; 1.20 mmol) was added via syringe and the solution was stirred vigorously at room temperature overnight. The reaction mixture was concentrated, dissolved in DMSO (3 ml), and purified via Reverse Phase chromatography (Yamazen, basic buffer) to provide 9 16? (46 mg; 43% yield) as the free base. LC-MS [354 (M+1)]

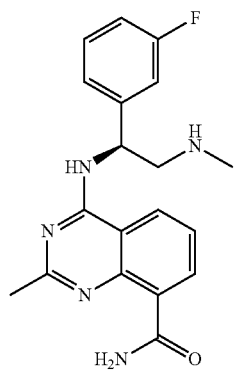

4-{[(1S)-1-(3-fluorophenyl)-2-(methylamino)ethyl]amino}-2-methylquinazoline-8-carboxamide (17)

IC$_{50}$ p70S6K [nM]: 139
This compound was prepared following the general procedure of example 16 using 1 and 10. LC-MS [354.2 (M+1)]

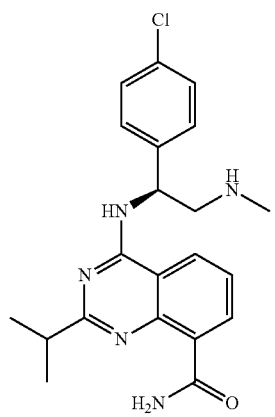 [SMILES: CNC[C@@H](Nc1nc(C(C)C)nc2c(C(N)=O)cccc12)c1ccc(Cl)cc1]

4-{[(1S)-1-(4-chlorophenyl)-2-(methylamino)ethyl]amino}-2-isopropylquinazoline-8-carboxamide (18)

IC$_{50}$ p70S6K [nM]: 23
This compound was prepared following the general procedure of example 16 using 3 and 8. LC-MS [398.2 (M+1)]

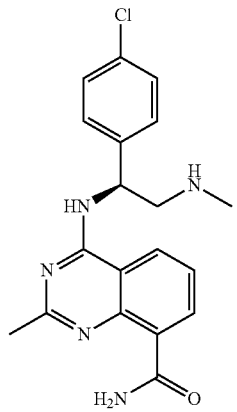

4-{[(1S)-1-(4-chlorophenyl)-2-(methylamino)ethyl]amino}-2-methylquinazoline-8-carboxamide (19)

IC$_{50}$ p70S6K [nM]: 0.83
This compound was prepared following the general procedure of example 16 using 1 and 8. LC-MS [370.2 (M+1)]

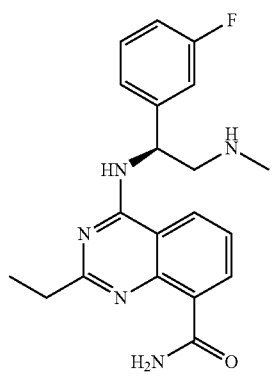

2-Ethyl-4-{[(1S)-1-(3-fluorophenyl)-2-(methylamino)ethyl]amino}quinazoline-8-carboxamide (20)

IC$_{50}$ p70S6K [nM]: 1.97
This compound was prepared following the general procedure of example 16 using 2 and 10. LC-MS [368.2 (M+1)]

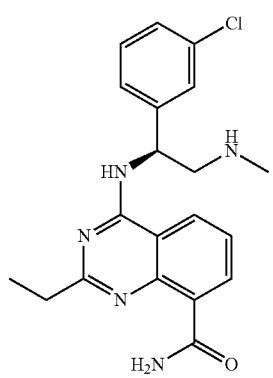 [SMILES: CCc1nc(N[C@H](CNC)c2cccc(F)c2)c2cccc(C(N)=O)c2n1]

4-{[(1S)-1-(3-Chlorophenyl)-2-(methylamino)ethyl]amino}-2-ethylquinazoline-8-carboxamide (21)

IC$_{50}$ p70S6K [nM]: 0.87
This compound was prepared following the general procedure of example 16 using 2 and 7. LC-MS [384.2 (M+1)]

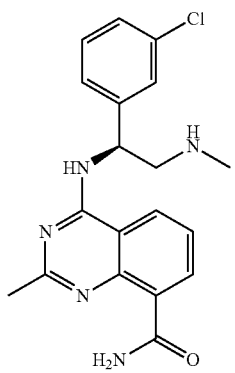

4-{[(1S)-1-(3-Chlorophenyl)-2-(methylamino)ethyl]amino}-2-methylquinazoline-8-carboxamide (22)

$IC_{50}$ p70S6K [nM]: 0.98
This compound was prepared following the general procedure of example 16 using 1 and 7. LC-MS [370.1 (M+1)]

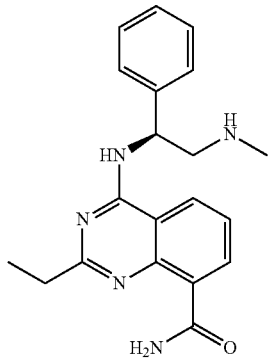 [SMILES: CCc1nc(N[C@H](CNC)c2ccccc2)c2cccc(C(N)=O)c2n1]

2-Ethyl-4-{[(1S)-2-(methylamino)-1-phenylethyl]amino}quinazoline-8-carboxamide (23)

$IC_{50}$ p70S6K [nM]: 11
This compound was prepared following the general procedure of example 16 using 2 and 5. LC-MS [350.2 (M+1)]

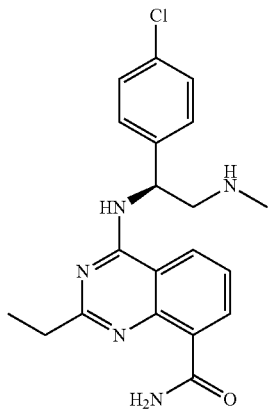 [SMILES: CCc1nc(N[C@H](CNC)c2ccc(Cl)cc2)c2cccc(C(N)=O)c2n1]

4-{[(1S)-1-(4-Chlorophenyl)-2-(methylamino)ethyl]amino}-2-ethylquinazoline-8-carboxamide (24)

$IC_{50}$ p70S6K [nM]: 1.4
This compound was prepared following the general procedure of example 16 using 2 and 8. LC-MS [384.2 (M+1)]

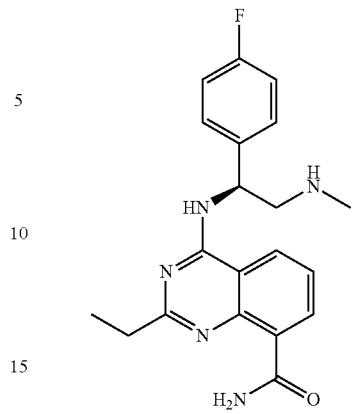

2-Ethyl-4-{[(1S)-1-(4-fluorophenyl)-2-(methylamino)ethyl]amino}quinazoline-8-carboxamide (25)

$IC_{50}$ p70S6K [nM]: 10
This compound was prepared following the general procedure of example 16 using 2 and 9. LC-MS [368.2 (M+1)]

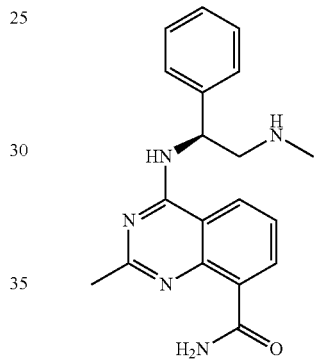

2-Methyl-4-{[(1S)-2-(methylamino)-1-phenylethyl]amino}quinazoline-8-carboxamide (26)

$IC_{50}$ p70S6K [nM]: 6.46
This compound was prepared following the general procedure of example 16 using 1 and 5. LC-MS [336 (M+1)]

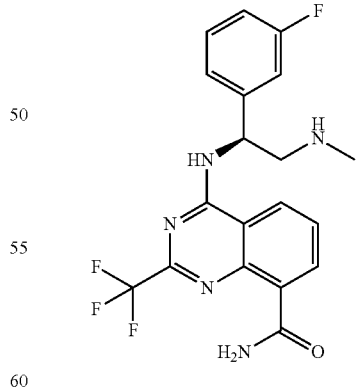

4-{[(1S)-1-(3-Fluorophenyl)-2-(methylamino)ethyl]amino}-2-(trifluoromethyl)-quinazoline-8-carboxamide (27)

$IC_{50}$ p70S6K [nM]: 4.3
This compound was prepared following the general procedure of example 16 using 4 and 10. LC-MS [408 (M+1)]

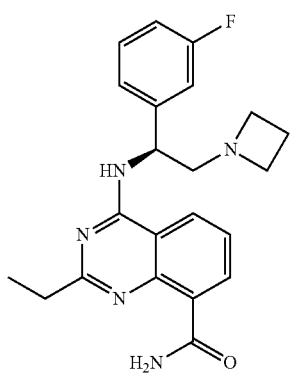 [SMILES: CCc1nc(N[C@H](CN2CCC2)c2cccc(F)c2)c2cccc(C(N)=O)c2n1]

4-[(S)-3-Azetidin-1-yl-2-(3-fluorophenyl)-propyl]-2-ethyl-quinazoline-8-carboxylic acid amide (28)

IC$_{50}$ p70S6K [nM]: 18.5

4-[(S)-3-Azetidin-1-yl-2-(3-fluorophenyl)-propyl]-2-ethyl-quinazoline-8-carboxylic acid methyl ester 2 (100 mg; 0.40 mmol), 11 (69 mg; 0.36 mmol; 0.90 eq.) and TEA (0.28 ml; 1.99 mmol) were dissolved in CH$_3$CN (6 mL) and stirred overnight. The reaction mixture was filtered and the filtrate was concentrated to provide the desired intermediate. LC-MS [409 (M+1)].

4-[(S)-3-Azetidin-1-yl-2-(3-fluorophenyl)-propyl]-2-ethyl-quinazoline-8-carboxylic acid amide Methyl 4-{[(1S)-2-azetidin-1-yl-1-(3-fluorophenyl)ethyl]amino}-2-ethylquinazoline-8-carboxylate (70.00 mg; 0.17 mmol) was suspended in methanolic ammonia (0.98 ml; 7.00 M; 6.85 mmol) and stirred for 24 h. The reaction mixture was concentrated, and the crude product was purified via silica gel flash chromatography (MeOH:EtOAc=1:9) to provide 28 (15 mg). LC-MS [394 (M+1)]. $^1$H NMR (DMSO-d$_6$, ppm) 1.21 (3H), 1.91 (2H), 2.50 (2H), 2.74 (3H), 3.00 (1H), 3.13 (2H), 5.50 (1H), 7.22 (1H), 7.30 (2H), 7.44 (2H), 7.54 (1H), 7.78 (1H), 8.56 (3H), 10.69 (1H).

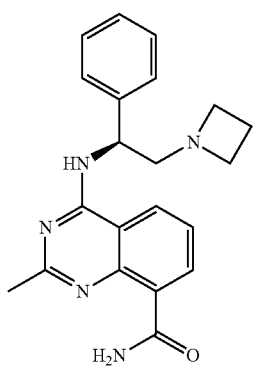 [SMILES: Cc1nc(N[C@H](CN2CCC2)c2ccccc2)c2cccc(C(N)=O)c2n1]

4-[(S)-3-Azetidin-1-yl-2-phenyl-propyl]-2-methyl-quinazoline-8-carboxylic acid amide (29)

IC$_{50}$ p70S6K [nM]: 5.84

This compound was prepared following the general procedure of example 28 using 1 and 12. LC-MS [362 (M+1)]. $^1$H NMR (DMSO-d$_6$, ppm) 1.90 (2H), 2.47 (5H), 2.74 (1H), 2.97 (1H), 3.16 (2H), 5.49 (1H), 7.22 (1H), 7.30 (4H), 7.44 (2H), 7.54 (1H), 7.78 (1H), 8.55 (3H), 10.69 (1H).

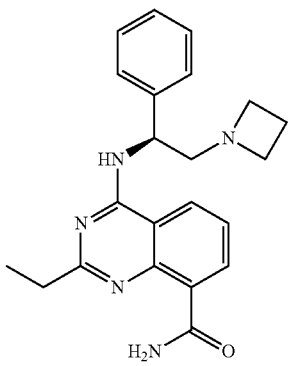 [SMILES: CCc1nc(N[C@H](CN2CCC2)c2ccccc2)c2cccc(C(N)=O)c2n1]

4-[(S)-3-Azetidin-1-yl-2-phenyl-propyl]-2-ethyl-quinazoline-8-carboxylic acid amide (30)

IC$_{50}$ p70S6K [nM]: 33.6

This compound was prepared following the general procedure of example 28 using 2 and 12. LCMS [376 (M+1)]. $^1$H NMR (DMSO-d$_6$, ppm) 1.21 (3H), 1.91 (2H), 2.50 (2H), 2.74 (3H), 3.00 (1H), 3.13 (2H), 5.50 (1H), 7.22 (1H), 7.30 (3H), 7.44 (2H), 7.54 (1H), 7.78 (1H), 8.56 (3H), 10.69 (1H).

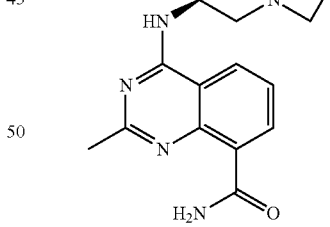

4-[(S)-3-Azetidin-1-yl-2-(4-chlorophenyl)-propyl]-2-methyl-quinazoline-8-carboxylic acid amide (31)

IC$_{50}$ p70S6K [nM]: 2.6

This compound was prepared following the general procedure of example 28 using 1 and 13. LC-MS [397 (M+1)]. $^1$H NMR (DMSO-d$_6$, ppm) 1.90 (2H), 2.46 (3H), 2.50 (2H), 2.74 (1H), 2.97 (1H), 3.16 (2H), 5.45 (1H), 7.47 (2H), 7.52 (1H), 7.78 (1H), 8.56 (3H), 10.55 (1H).

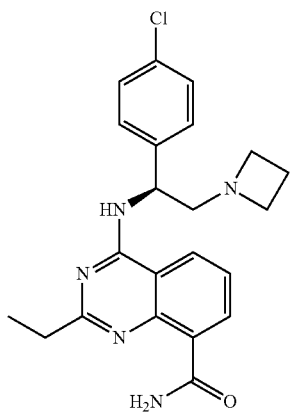 [SMILES: CCc1nc(N[C@H](CN2CCC2)c2ccc(Cl)cc2)c2cccc(C(N)=O)c2n1]

4-[(S)-3-Azetidin-1-yl-2-(4-chlorophenyl)-propyl]-2-ethyl-quinazoline-8-carboxylic acid amide (32)

IC$_{50}$ p70S6K [nM]: 5.5

This compound was prepared following the general procedure of example 28 using 2 and 13. LCMS [411 (M+1)]. $^1$H NMR (DMSO-d$_6$, ppm) 1.21 (3H), 1.91 (2H), 2.5 (1H), 2.73 (3H), 2.98 (1H), 3.13 (3H), 5.43 (1H), 7.37 (3H), 7.47 (2H), 7.78 (1H), 8.56 (3H), 10.66 (1H).

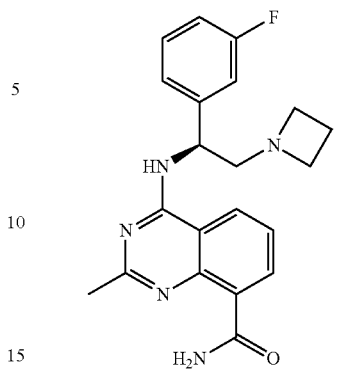

4-[(S)-3-Azetidin-1-yl-2-(3-fluorophenyl)-propyl]-2-methyl-quinazoline-8-carboxylic acid amide (34)

IC$_{50}$ p70S6K [nM]: 7

This compound was prepared following the general procedure of example 28 using 1 and 11. LC-MS [380 (M+1)]. $^1$H NMR (DMSO-d$_6$, ppm) 1.91 (2H), 2.4821 (5H), 2.75 (1H), 2.98 (1H), 3.16 (2H), 5.49 (1H), 7.47 (2H), 7.52 (1H), 7.78 (1H), 8.56 (3H), 10.55 (1H).

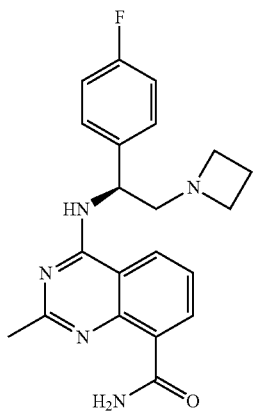 [SMILES: Cc1nc(N[C@H](CN2CCC2)c2ccc(F)cc2)c2cccc(C(N)=O)c2n1]

4-[(S)-3-Azetidin-1-yl-2-(4-fluorophenyl)-propyl]-2-methyl-quinazoline-8-carboxylic acid amide (33)

IC$_{50}$ p70S6K [nM]: 44

This compound was prepared following the general procedure of example 28 using 1 and 14. LCMS [380 (M+1)]. $^1$H NMR (DMSO-d$_6$, ppm) 1.90 (2H), 2.47 (5H), 2.7461 (1H), 2.97 (1H), 3.16 (2H), 5.49 (1H), 7.47 (2H), 7.52 (1H), 7.78 (1H), 8.56 (3H), 10.55 (1H).

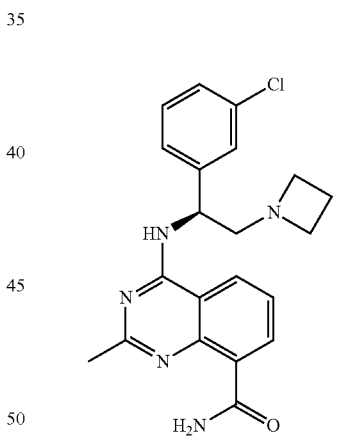

4-[(S)-3-Azetidin-1-yl-2-(3-chlorophenyl)-propyl]-2-methyl-quinazoline-8-carboxylic acid amide (35)

IC$_{50}$ p70S6K [nM]: 1.3

This compound was prepared following the general procedure of example 28 using 1 and 15. LC-MS [396 (M+1)]. $^1$H NMR (DMSO-d$_6$, ppm) 1.91 (2H), 2.48 (5H), 2.74 (1H), 2.98 (1H), 3.16 (2H), 5.49 (1H), 7.47 (2H), 7.52 (1H), 7.78 (1H), 8.56 (3H), 10.55 (1H).

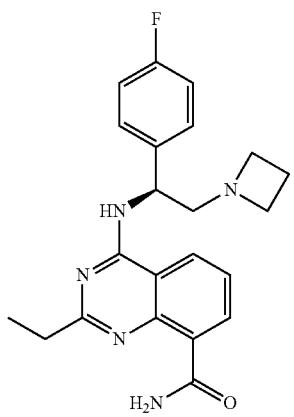

4-[(S)-3-Azetidin-1-yl-2-(4-fluorophenyl)-propyl]-2-ethyl-quinazoline-8-carboxylic acid amide (36)

IC$_{50}$ p70S6K [nM]: 30
This compound was prepared following the general procedure of example 28 using 2 and 14. LC-MS [394 (M+1)]. $^1$H NMR (DMSO-d$_6$, ppm) 1.21 (3H), 1.99 (2H), 2.50 (1H), 2.73 (3H), 2.98 (1H), 3.13 (3H), 5.43 (1H), 7.37 (3H), 7.47 (2H), 7.78 (1H), 8.56 (3H), 10.66 (1H).

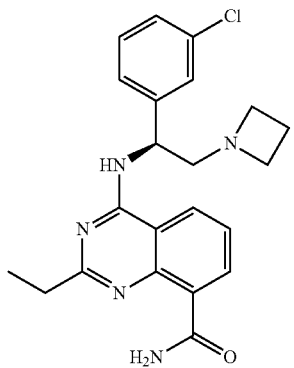

4-[(S)-3-Azetidin-1-yl-2-(3-chlorophenyl)-propyl]-2-ethyl-quinazoline-8-carboxylic acid amide (37)

IC$_{50}$ p70S6K [nM]: 1.7
This compound was prepared following the general procedure of example 28 using 2 and 15. LC-MS [410 (M+1)]. $^1$H NMR (DMSO-d$_6$, ppm) 1.23 (3H), 1.94 (2H), 2.50 (1H), 2.75 (3H), 2.98 (1H), 3.20 (3H), 5.43 (1H), 7.35 (3H), 7.44 (2H), 7.78 (1H), 8.53 (3H), 10.64 (1H).
Synthesis Intermediates

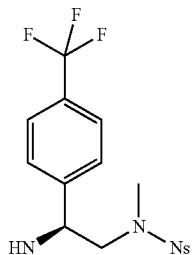

N-[(2S)-2-amino-2-(4-trifluoromethyl-phenyl)ethyl]-N-methyl-4-nitrobenzenesulfonamide (38)

This compound was prepared following the general procedure of example 5 using N-methyl-4-nitrobenzenesulfonamide and the corresponding amino alcohol. LC-MS [404 (M+1)]

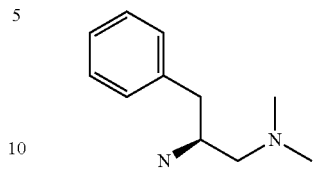

(S)—N$^1$,N$^1$-Dimethyl-3-phenylpropane-1,2-diamine (39)

This compound was prepared following the general procedure of example 5 using dimethylamine and the corresponding amino alcohol. LC-MS [179 (M+1)]

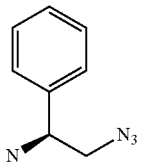 [SMILES: [N-]=[N+]=NC[C@@H](N)c1ccccc1]

(S)-2-Azido-1-phenyl-ethylamine (40)

To a solution of tert-butyl [(1S)-phenyl)-2-hydroxyethyl] carbamate (237 mg, 1.0 mmol, 1.0 eq.) and TEA (278 μl; 2.0 mmol; 2.0 eq.) in DCM (5 ml) at 0° C., 4-methylbenzenesulfonyl chloride (210 mg, 1.1 mmol, 1.1 eq.) was added in portion. The resulting mixture was stirred at room temperature overnight. The reaction mixture was diluted with ethyl acetate and washed with saturated sodium bicarbonate and brine. The organic layer was dried over MgSO$_4$ and concentrated. The crude was purified by Biotage with 0-30% ethyl acetate in hexane to afford (2S)-2-[(tert-butoxycarbonyl)amino]-2-phenylethyl 4-methylbenzenesulfonate as a white solid in 93% yield.

The mixture of (2S)-2-[(tert-butoxycarbonyl)amino]-2-phenylethyl 4-methylbenzenesulfonate (350 mg, 0.9 mmol, 1.0 eq.) and sodium azide (117 mg, 1.8 mmol, 2.0 eq.) in N,N-dimethylformamide (5 ml) was stirred at 65° C. overnight. The mixture was cooled to room temperature and diluted with water and ethyl acetate. The organic layer was separated and washed with brine, dried, and concentrated to afford tert-butyl [(1S)-2-azido-1-phenylethyl]carbamate in 90% yield.

To a solution of tert-butyl [(1S)-2-azido-1-phenylethyl] carbamate (210 mg, 0.8 mmol, 1.0 eq.) in THF (2 ml), 4.0M hydrogen chloride in dioxane (2.0 ml, 8.0 mmol, 10.0 eq.) was added. The reaction mixture was stirred at room temperature overnight. The reaction mixture was diluted with ether. The precipitate was filtered and washed with ether to yield (S)-2-Azido-1-phenyl-ethylamine 40 as a white solid in 85% yield. LC-MS [163 (M+1)]

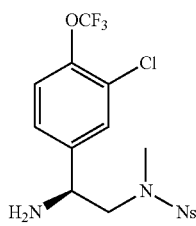

(S)—N-(2-amino-2-(3-chloro-4-(trifluoromethoxy)phenyl)ethyl)-N-methyl-4-nitrobenzenesulfonamide (41)

This compound was prepared following the general procedure of example 5 using N-methyl-4-nitrobenzenesulfonamide and the corresponding amino alcohol. LC-MS [454 (M+1)]

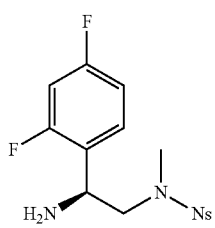

(S)—N-(2-amino-2-(2,4-difluorophenyl)ethyl)-N-methyl-4-nitrobenzenesulfonamide (42)

This compound was prepared following the general procedure of example 5 using N-methyl-4-nitrobenzenesulfonamide and the corresponding amino alcohol. LC-MS [372 (M+1)]

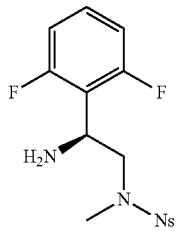

(S)—N-(2-amino-2-(2,6-difluorophenyl)ethyl)-N-methyl-4-nitrobenzenesulfonamide (43)

This compound was prepared following the general procedure of example 5 using N-methyl-4-nitrobenzenesulfonamide and the corresponding amino alcohol. LC-MS [372 (M+1)]

(S)—N-(2-amino-2-(2,5-difluorophenyl)ethyl)-N-methyl-4-nitrobenzenesulfonamide (44)

This compound was prepared following the general procedure of example 5 using N-methyl-4-nitrobenzenesulfonamide and the corresponding amino alcohol. LC-MS [372 (M+1)]

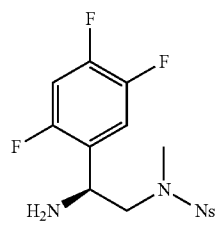

(S)—N-(2-amino-2-(2,4,5-trifluorophenyl)ethyl)-N-methyl-4-nitrobenzene-sulfonamide (45)

This compound was prepared following the general procedure of example 5 using N-methyl-4-nitrobenzenesulfonamide and the corresponding amino alcohol. LC-MS [390 (M+1)]

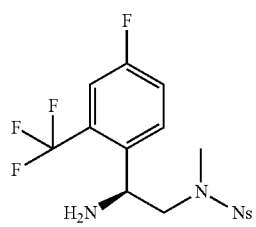

(S)-1-(4-Fluoro-2-trifluoromethyl-phenyl)-N*2*,N*2*-dimethyl-ethane-1,2-diamine (46)

This compound was prepared following the general procedure of example 5 using N-methyl-4-nitrobenzenesulfonamide and the corresponding amino alcohol. LC-MS [422 (M+1)]

Example Compounds According to Formula (I)

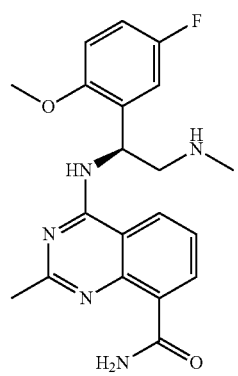

4-[(S)-1-(5-Fluoro-2-methoxy-phenyl)-2-methylamino-ethylamino]-2-methyl-quinazoline-8-carboxylic acid amide (47)

IC$_{50}$ p70S6K [nM]: 12

This compound was prepared following the general procedure of example 16 using 1 and 6. LC-MS [384 (M+1)].

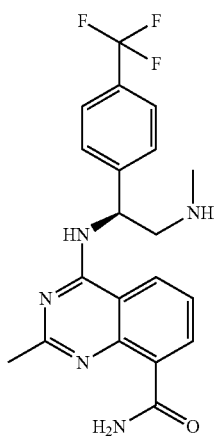

2-Methyl-4-[(S)-2-methylamino-1-(4-trifluoromethyl-phenyl)-ethylamino]-quinazoline-8-carboxylic acid amide (48)

IC$_{50}$ p70S6K [nM]: 1
This compound was prepared following the general procedure of example 16 using 1 and 38. LC-MS [404 (M+1)].

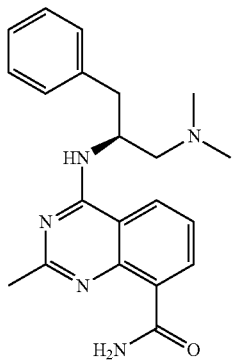

4-((S)-1-Benzyl-2-dimethylamino-ethylamino)-2-methyl-quinazoline-8-carboxylic acid amide (49)

IC$_{50}$ p70S6K [nM]: 452
This compound was prepared following the general procedure of example 16 using 1 and 39. LC-MS [364 (M+1)].

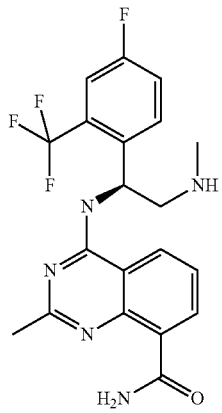

4-[(1S)-1-[4-fluoro-2-(trifluoromethyl)phenyl]-2-(methylamino)ethyl]amino-2-methylquinazoline-8-carboxamide (50)

IC$_{50}$ p70S6K [nM]: 260
This compound was prepared following the general procedure of example 16 using 1 and 46. LC-MS [422 (M+1)].

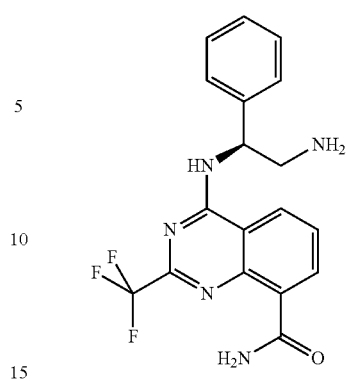

4-((S)-2-Amino-1-phenyl-ethylamino)-2-trifluoromethyl-quinazoline-8-carboxylic acid amide (51)

IC$_{50}$ p70S6K [nM]: 8

To a solution of the chloride 4 (175 mg, 0.60 mmol) and N,N-diisopropylethylamine (0.53 mL, 3.0 mmol) in tetrahydrofuran (8.0 mL) was added the amine 40 (132 mg, 0.66 mmol) and the reaction was heated to 65° C. for 16 hours. The reaction was diluted with saturated sodium chloride and ethyl acetate was added. The biphasic mixture was extracted three times with ethyl acetate and the combined extracts were dried over sodium sulfate. Column chromatography of the resulting residue (dichloromethane to 10% methanol in dichloromethane) gave the product as a pale yellow foam, LCMS (ESI) 417 (M+H). This material was dissolved in isopropanol (5.0 mL) and ammonium hydroxide (10.0 mL) was added slowly and the reaction was stirred for 16 hours at room temperature. The total volume of the reaction was reduced to ¼ in vacuo and this solution was diluted with saturated sodium bicarbonate and ethyl acetate. The biphasic solution was extracted three times with ethyl acetate and the combined organics were dried over sodium sulfate. The extract was concentrated to the crude 4-((S)-2-azido-1-phenyl-ethylamino)-2-trifluoromethyl-quinazoline-8-carboxylic acid amide whose main peak exhibited the correct m/z by LC/MS analysis, LCMS (ESI) 402 (M+H).

The crude azide was dissolved in ethanol (15 mL) and a catalytic amount of 5% palladium on carbon was added. The heterogenous solution was stirred for 2 hours under an atmosphere of hydrogen and then the suspension was filtered through a pad of Celite and the filtrate was concentrated to a pale yellow film. This material was re-dissolved in tetrahydrofuran (5.0 mL) and treated with 4 N hydrochloric acid in dioxane (4.0 mL) for 15 minutes. The reaction was then concentrated to dryness and the resulting solid was triturated three times with diethyl ether to provide the title compound (HCl salt) as a pale yellow powder (202 mg) in 57% over the previous four steps. LC-MS [376 (M+1)]. 1H NMR (400 MHz, DMSO-d$_6$) δ ppm 3.19-3.38 (m, 1 H) 3.67-3.89 (m, 1 H) 5.76 (br. s., 1 H) 7.31 (d, J=7.42 Hz, 1 H) 7.38 (t, J=7.52 Hz, 2 H) 7.55 (d, J=7.32 Hz, 2 H) 7.84 (t, J=7.86 Hz, 1 H) 7.89-8.06 (m, 1 H) 8.63 (dd, J=7.52, 1.37 Hz, 1 H) 9.01 (d, J=8.40 Hz, 2 H) 9.48 (br. s., 1 H) 9.90 (s, 1 H).

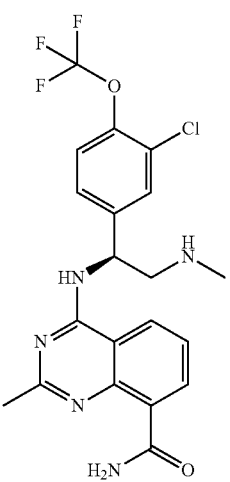

(S)-4-(1-(3-chloro-4-(trifluoromethoxy)phenyl)-2-(methylamino)ethyl)amino)-2-methylquinazoline-8-carboxamide (52)

IC$_{50}$ p70S6K [nM]: 1

(S)-methyl 4-((2-(4-amino-N-methylphenylsulfonamido)-1-(3-chloro-4-(trifluoromethoxy)phenyl)ethyl)amino)-2-methylquinazoline-8-carboxylate To a solution of methyl 2-methyl-4-oxo-3,4-dihydroquinazoline-8-carboxylate (91.65 mg; 0.42 mmol; 1.20 eq.) in NMP (3 mL) was added 1,8-diazabicyclo[5.4.0]undec-7-ene (104.58 µl; 0.70 mmol; 2.00 eq.). The solution was stirred at room temperature for 5 minutes and then PyBOP (273.21 mg; 0.52 mmol; 1.50 eq.) was added and stirred for 10 minutes before adding a solution of N-(2S)-2-amino-2-[3-chloro-4-(trifluoromethoxy)phenyl]ethyl-N-methyl-4-nitrobenzenesulfonamide hydrochloride 41 (171.60 mg; 0.35 mmol; 1.00 eq.) and N-ethyl-N-isopropylpropan-2-amine (60.96 µl; 0.35 mmol; 1.00 eq.) in NMP (1 mL). The reaction mixture was stirred at room temperature overnight.

After 14 hr the reaction was diluted with water and purified via prep HPLC to yield 110 mg (41%) of (S)-methyl 4-((2-(4-amino-N-methylphenylsulfonamido)-1-(3-chloro-4-(trifluoromethoxy)phenyl)ethyl)amino)-2-methylquinazoline-8-carboxylate. LC-MS [655 (M+1)]

(S)-4-((2-(4-amino-N-methylphenylsulfonamido)-1-(3-chloro-4-(trifluoromethoxy)phenyl)ethyl)amino)-2-methylquinazoline-8-carboxamide To a reaction vial with magnetic stirbar was added methyl 4-[((1S)-1-[3-chloro-4-(trifluoromethoxy)phenyl]-2-methyl[(4-nitrophenyl)sulfonyl]aminoethyl)amino]-2-methylquinazoline-8-carboxylate trifluoroacetate (268.82 mg; 0.35 mmol; 1.00 eq.), DMSO (2 mL), IPA (2 mL), and concentrated NH$_4$OH (2 mL). The vessel was sealed and the reaction was stirred at 70 degrees C. overnight.

The reaction was worked up (EA/water) and then concentrated to yield 80 mg (36%) of the crude intermediate. LC-MS [640 (M+1)]

(S)-4-((1-(3-chloro-4-(trifluoromethoxy)phenyl)-2-(dimethylamino)ethyl)amino)-2-methylquinazoline-8-carboxamide Crude (S)-4-((2-(4-amino-N-methylphenylsulfonamido)-1-(3-chloro-4-(trifluoromethoxy)phenyl)ethyl)amino)-2-methylquinazoline-8-carboxamide (80.00 mg; 0.13 mmol; 1.00 eq.) was dissolved into acetonitrile (4.0 ml). Cesium carbonate (245 mg, 6.0 eq) was added and the suspension was stirred for 10 minutes. Benzenethiol (51.18 µl; 0.50 mmol; 4.00 eq.) was added via syringe and the solution was stirred vigorously at room temperature overnight. Water (3 mL) was added and the homogeneous reaction was purified directly via prep. HPLC to yield 28 mg (41%) of compound 52. LC-MS [454 (M+1)]

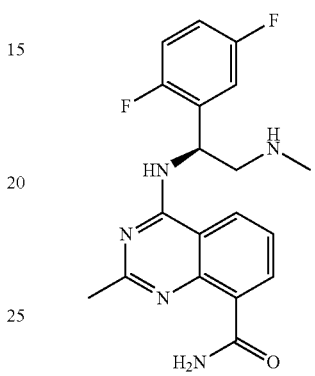

(S)-4-(1-(2,5-difluorophenyl)-2-(methylamino)ethyl)amino)-2-methylquinazoline-8-carboxamide (53)

IC$_{50}$ p70S6K [nM]: 3

This compound was prepared following the general procedure of example 52 using 1 and 44. LC-MS [372 (M+1)]

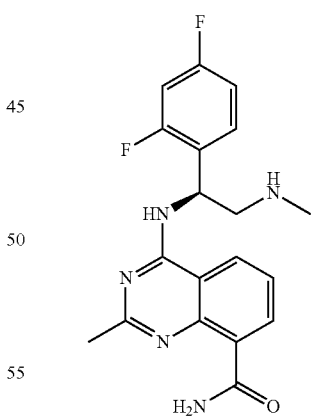

(S)-4-(1-(2,4-difluorophenyl)-2-(methylamino)ethyl)amino)-2-methylquinazoline-8-carboxamide (54)

IC$_{50}$ p70S6K [nM]: 7

This compound was prepared following the general procedure of example 52 using 1 and 42. LC-MS [372 (M+1)]

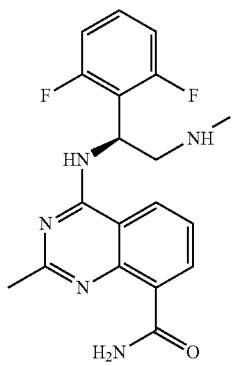

(S)-4-(1-(2,6-difluorophenyl)-2-(methylamino)ethyl)amino)-2-methylquinazoline-8-carboxamide (55)

IC$_{50}$ p70S6K [nM]: 6
This compound was prepared following the general procedure of example 52 using 1 and 43. LC-MS [372 (M+1)]

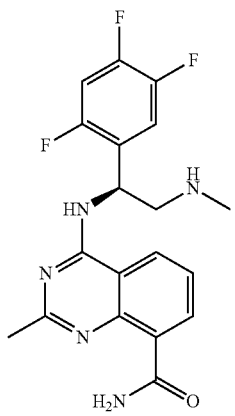

(S)-2-methyl-4-((2-(methylamino)-1-(2,4,5-trifluorophenyl)ethyl)amino)quinazoline-8-carboxamide (56)

IC$_{50}$ p70S6K [nM]: 1
This compound was prepared following the general procedure of example 52 using 1 and 45. LC-MS [390 (M+1)]

Synthesis Intermediates

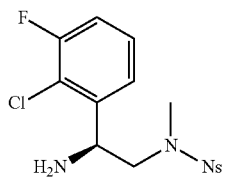

N-(2S)-amino-2-(2-chloro-3-fluorophenyl)ethyl)-N-methyl-4-nitrobenzene-sulfonamide (57)

This compound was prepared following the general procedure of example 5 using N-methyl-4-nitrobenzenesulfonamide and the corresponding amino alcohol. LC-MS [388.1 (M+1)]

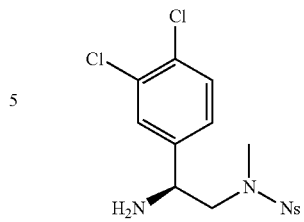

N-(2S)-amino-2-(3,4-dichlorophenyl)ethyl)-N-methyl-4-nitrobenzenesulfonamide (58)

This compound was prepared following the general procedure of example 5 using N-methyl-4-nitrobenzenesulfonamide and the corresponding amino alcohol. LC-MS [404.1 (M+1)]

Example Compounds According to Formula (I)

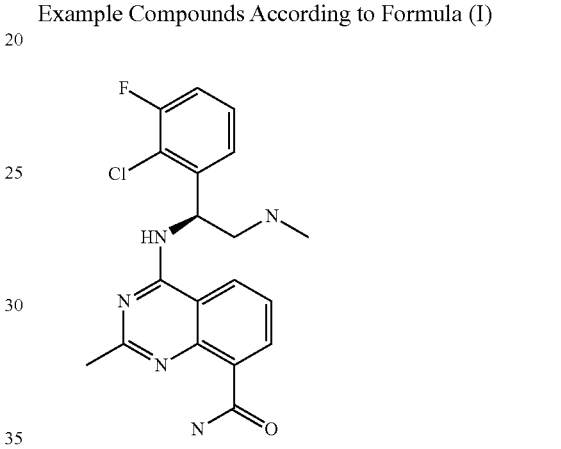

(S)-4-((1-(2-chloro-3-fluorophenyl)-2-(methylamino)ethyl)amino)-2-methylquinazoline-8-carboxamide (59)

This compound was prepared following the general procedure of example 16 using 1 and 57. LC-MS [370.2 (M+1)]

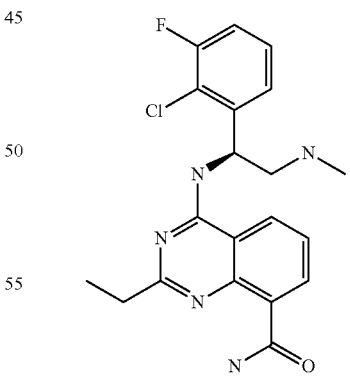

(S)-4-((1-(2-chloro-3-fluorophenyl)-2-(methylamino)ethyl)amino)-2-ethylquinazoline-8-carboxamide (60)

IC$_{50}$ p70S6K [nM]: 9
This compound was prepared following the general procedure of example 16 using 2 and 57. LC-MS [402.4 (M+1)]

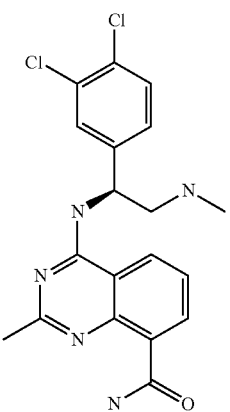

(S)-4-(1-(3,4-dichlorophenyl)-2-(methylamino)ethyl)amino)-2-methylquinazoline-8-carboxamide (61)

IC$_{50}$ p70S6K [nM]: 330

This compound was prepared following the general procedure of example 16 using 1 and 58. LC-MS [404.4 (M+1)]

Biological Activity

P70S6K Enzyme Assay

P70S6K inhibitor compounds are diluted and plated in 96 well plates. A reaction mixture including the following components is then added to the compound plate to initiate the enzyme reaction; P70S6K (3 nM, T412E mutant, Millipore) is mixed with 24 μM ATP in an assay buffer containing 100 mM Hepes (pH 7.5), 5 mM MgCl$_2$, 1 mM DTT, 0.015% Brij and 1 μM of the substrate peptide FITC-AHA-AKRRRLSS-LRA-OH (derived from the S6 ribosomal protein sequence, FITC=fluorescein isothiocyanate, AHA=6-aminohexanoic acid). The reaction is incubated for 90 min at 25° C., before the addition of 10 mM EDTA to stop the reaction. The proportion of substrate and product (phosphorylated) peptide is analysed on a Caliper Life Sciences Lab Chip 3000, using a pressure of −1.4 psi, and upstream and downstream voltages of −3000 and −700 respectively. Product peaks are resolved before substrate peaks on the resulting chromatograms.

To assess the inhibitory potential of the compounds, IC$_{50}$-values were determined, as shown in Chemical Synthesis section above.

The invention claimed is:

1. A compound of Formula (I)

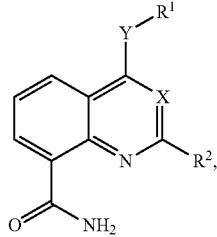

(I)

and pharmaceutically acceptable salts, thereof, wherein:
X is N,
Y is NH, O or absent,
R$^1$ is L$^1$-R$^4$-L$^2$-R$^5$ or L$^1$-R$^4$,
R$^2$ is A, Hal, OH, OA, SH, CN, NH$_2$, NO$_2$, NHA, NH-L$^1$-Ar, NHCOA, NHCO-L-$^1$-Ar, NHSO$_2$A, NHSO$_2$-L$^1$-Ar, NHCONHA, NHCONH-L$^1$-Ar, L$^1$-Ar, O-L$^1$-Ar, L$^1$-R$^4$,
L$^1$ is a single bond, methylene, or methyl substituted methylene, wherein the methylene, or the methyl group of the methyl substituted methylene may be unsubstituted or mono- or disubstituted with Hal, OH, CN, NH$_2$, NH(LA), N(LA)$_2$, NO$_2$, COOH, N$_3$, ethenyl or ethynyl, and/or monosubstituted with R$^4$, and in which one or two CH$_2$ groups may be replaced by an O or S atom or by an —NH—, —N(LA)-, —CONH—, —N(LA)COO—, —SO$_2$— or —NHCO— group,
R$^3$ is H, A, Hal, OH, COOH, SH, NH$_2$, NO$_2$ or CN,
R$^4$, R$^5$ each, independently of one another, are Ar, or cyclic A which may be mono- or disubstituted by Hal or LA,
L$^2$ is —NHCO—, —NHCOO—, —NHCONH—, —NH-CONA-, —NHCOA—, —O—, —S—, —NH—, —NHSO$_2$—, —SO$_2$NH—, —CONH—, —CONH-CONH—, —NHCONHCO—, or -A-,
Ar is a mono- or bicyclic aromatic homo- or heterocycle having 0, 1, 2, 3 or 4 N, O and/or S atoms and 5, 6, 7, 8, 9, or 10 skeleton atoms, which may be unsubstituted or, independently of one another, mono-, di- or trisubstituted by Hal, A, OH, SH, OA, NH$_2$, NHA, NA$_2$, NO$_2$, CN, OCN, SCN, COOH, COOA, CONH$_2$, CONHA, CONA$_2$, NHCOA, NHCONHA, NHCONH$_2$, NHSO$_2$A, CHO, COA, SO$_2$NH$_2$, SO$_2$A and/or SO$_2$Hal, and in which a ring N-atom may be substituted by an O-atom to form an N-oxide group, and in which in the case of a bicyclic aromatic cycle on of the two rings may be partly saturated,
A is unbranched or branched linear or cyclic alkyl having 1, 2, 3, 4, 5, 6, 7 or 8 C atoms, in which one or two CH$_2$ groups may be replaced by an O or S atom and/or by an —NH—, —CO—, —NHCOO—, —NHCONH—, —N(LA)-, —CONH—, —NHCO— or —CH=CH— group, and in which 1-3 H atoms may be replaced by Hal, and in which one or two CH$_3$ groups may be replaced by OH, SH, NH$_2$, NH(LA), N(LA)$_2$, NHCOOH, NHCONH$_2$ or CN,
LA is unbranched or branched, linear alkyl having 1, 2, 3 or 4 C atoms, wherein 1, 2 or 3 H atoms may be replaced by Hal,
Hal is F, Cl, Br or I.

2. The compound according to claim 1 and pharmaceutically acceptable salts thereof, wherein:
X is N,
Y is NH,
R$^1$ is L$^1$-R$^4$,
R$^2$ is LA, Hal, OH, O(LA), SH, CN, NH$_2$, NO$_2$, NH(LA), NHCO(LA), NHSO$_2$(LA), NHCONH(LA),
L$^1$ is methyl substituted methylene, wherein the methyl group of the methyl substituted methylene is monosubstituted with NH$_2$ or NH(LA), N(LA)$_2$, or cyclic A which may be mono- or disubstituted by Hal or LA,
R$^4$ is a monocyclic aromatic homo- or heterocycle having 0, 1 or 2 N, O and/or S atoms and 5 or 6 skeleton atoms, which may be unsubstituted or, independently of one another, mono-, di- or trisubstituted by Hal, A, OH, SH, OA, NH$_2$, NHA, NA$_2$, NO$_2$, CN, OCN, SCN, COOH, COOA, CONH$_2$, CONHA, CONA$_2$, NHCOA, NHCONHA, NHCONH$_2$, NHSO$_2$A, CHO, COA, SO$_2$NH$_2$, SO$_2$A and/or SO$_2$Hal,
A is unbranched or branched linear or cyclic alkyl having 1, 2, 3, 4, 5, 6, 7 or 8 C atoms, in which one or two CH$_2$ groups may be replaced by an O or S atom and/or by an —NH—, —CO—, —NHCOO—, —NHCONH—, —N(LA)-, —CONH—, —NHCO— or —CH=CH— group, and in which 1-3 H atoms may be replaced by Hal, and in which one or two $CH_3$ groups may be replaced by OH, SH, $NH_2$, NH(LA), $N(LA)_2$, NHCOOH, $NHCONH_2$ or CN, LA is unbranched or branched, linear alkyl having 1, 2, 3 or 4 C atoms, wherein 1, 2 or 3 H atoms may be replaced by Hal, Hal is F, Cl, Br or I.

3. The compound according to claim 2, in which the residues not designated in greater detail have the meaning indicated in claim 2, but in which in Subformula 1
$R^2$ is LA,
in Subformula 2
$L^1$ is methyl substituted methylene, wherein the methyl group of the methyl substituted methylene is monosubstituted with methylamino, dimethylamino or azetidine,
in Subformula 3
$R^4$ is phenyl which is unsubstituted or monosubstituted with Hal,
in Subformula 4
$R^2$ is methyl, ethyl, isopropyl or trifluoromethyl,
in Subformula 5
$L^1$ is methyl substituted methylene, wherein the methyl group of the methyl substituted methylene is monosubstituted with methylamino,
in Subformula 6
$L^1$ is methyl substituted methylene, wherein the methyl group of the methyl substituted methylene is monosubstituted with azetidin-1-yl,
in Subformula 7
$R^4$ is phenyl which is unsubstituted,
in Subformula 8
$R^4$ is phenyl which is meta or para substituted with F or Cl,
in Subformula 9
$R^2$ is LA,
$L^1$ is methyl substituted methylene, wherein the methyl group of the methyl substituted methylene is monosubstituted with methylamino or azetidine,
in Subformula 10
$R^2$ is LA,
$R^4$ is phenyl which is unsubstituted or monosubstituted with Hal,
in Subformula 11
$L^1$ is methyl substituted methylene, wherein the methyl group of the methyl substituted methylene is monosubstituted with methylamino or azetidine,
$R^4$ is phenyl which is unsubstituted or monosubstituted with Hal,
in Subformula 12
$R^2$ is LA,
$L^1$ is methyl substituted methylene, wherein the methyl group of the methyl substituted methylene is monosubstituted with methylamino or azetidine,
$R^4$ is phenyl which is unsubstituted or monosubstituted with Hal,
in Subformula 13
$R^2$ is methyl, ethyl, isopropyl or trifluoromethyl,
$L^1$ is methyl substituted methylene, wherein the methyl group of the methyl substituted methylene is monosubstituted with methylamino or azetidine,
$R^4$ is phenyl which is unsubstituted or monosubstituted with Hal,
in Subformula 14
$R^2$ is LA,
$L^1$ is methyl substituted methylene, wherein the methyl group of the methyl substituted methylene is monosubstituted with methylamino or azetidine,
$R^4$ is phenyl which is meta or para substituted with F or Cl,
in Subformula 15
$R^2$ is methyl, ethyl, isopropyl or trifluoromethyl,
$L^1$ is methyl substituted methylene, wherein the methyl group of the methyl substituted methylene is monosubstituted with methylamino or azetidine,
$R^4$ is phenyl which is meta or para substituted with F or Cl,
in Subformula 16
$R^2$ is methyl, ethyl, isopropyl or trifluoromethyl,
$L^1$ is methyl substituted methylene, wherein the methyl group of the methyl substituted methylene is monosubstituted with methylamino,
$R^4$ is phenyl which is meta or para substituted with F or Cl,
in Subformula 17
$R^2$ is methyl, ethyl, isopropyl or trifluoromethyl,
$L^1$ is methyl substituted methylene, wherein the methyl group of the methyl substituted methylene is monosubstituted with azetidin-1-yl,
$R^4$ is phenyl which is meta or para substituted with F or Cl,
in Subformula 18
$R^2$ is methyl, ethyl, isopropyl or trifluoromethyl,
$L^1$ is methyl substituted methylene, wherein the methyl group of the methyl substituted methylene is monosubstituted with methylamino or azetidine,
$R^4$ is phenyl which is meta substituted with F or Cl,
in Subformula 19
$R^2$ is methyl, ethyl, isopropyl or trifluoromethyl,
$L^1$ is methyl substituted methylene, wherein the methyl group of the methyl substituted methylene is monosubstituted with methylamino or azetidin-1-yl,
$R^4$ is phenyl which is meta substituted with F or Cl,
and pharmaceutically acceptable salts thereof.

4. The compound according to claim 1, wherein the compound is selected from the group consisting of:

4-{[(1S)-1-(4-fluorophenyl)-2-(methylamino)ethyl]amino}-2-methylquinazoline-8-carboxamide, 4-{[(1S)-1-(3-fluorophenyl)-2-(methylamino)ethyl]amino}-2-methylquinazoline-8-carboxamide, 4-{[(1S)-1-(4-chlorophenyl)-2-(methylamino)ethyl]amino}-2-isopropylquinazoline-8-carboxamide, 4-{[(1S)-1-(4-chlorophenyl)-2-(methylamino)ethyl]amino}-2-methylquinazoline-8-carboxamide, 2-Ethyl-4-{[(1S)-1-(3-fluorophenyl)-2-(methylamino)ethyl]amino}quinazoline-8-carboxamide, 4-{[(1S)-1-(3-Chlorophenyl)-2-(methylamino)ethyl]amino}-2-ethylquinazoline-8-carboxamide, 4-{[(1S)-1-(3-Chlorophenyl)-2-(methylamino)ethyl]amino}-2-methylquinazoline-8-carboxamide, 2-Ethyl-4-{[(1S)-2-(methylamino)-1-phenylethyl]amino}quinazoline-8-carboxamide 4-{[(1S)-1-(4-Chlorophenyl)-2-(methylamino)ethyl]amino}-2-ethylquinazoline-8-carboxamide, 2-Ethyl-4-{[(1S)-1-(4-fluorophenyl)-2-(methylamino)ethyl]amino}quinazoline-8-carboxamide, 2-Methyl-4-{[(1S)-2-(methylamino)-1-phenylethyl]amino}quinazoline-8-carboxamide 4-{[(1S)-1-(3-Fluorophenyl)-2-(methylamino)ethyl]amino}-2-(trifluoromethyl)-quinazoline-8-carboxamide, 4-[(S)-3-Azetidin-1-yl-2-(3-fluorophenyl)-propyl]-2-ethyl-quinazoline-8-carboxylic acid amide, 4-[(S)-3-Azetidin-1-yl-2-phenyl-propyl]-2-methyl-quinazoline-8-carboxylic acid amide 4-[(S)-3-Azetidin-1-yl-2-phenyl-propyl]-2-ethyl-quinazoline-8-carboxylic acid amide 4-[(S)-3-Azetidin-1-yl-2-(4-chlorophenyl)-propyl]-2-methyl-quinazoline-8-carboxylic acid amide, 4-[(S)-3-Azetidin-1-yl-2-(4-chlorophenyl)-propyl]-2-ethyl-quinazoline-8-carboxylic acid amide, 4-[(S)-3-Azetidin-1-yl-2-(4-fluorophenyl)-propyl]-2-methyl-quinazoline-8-carboxylic acid amide, 4-[(S)-3-Azetidin-1-yl-2-(3-fluorophenyl)-propyl]-2-methyl-quinazoline-8-carboxylic acid amide, 4-[(S)-3-Azetidin-1-yl-2-(3-chlorophenyl)-propyl]-2-methyl-quinazoline-8-carboxylic acid amide, 4-[(S)-3-Azetidin-1-yl-2-(4-fluorophenyl)-propyl]-2-ethyl-quinazoline-8-carboxylic acid amide, 4-[(S)-3-Azetidin-1-yl-2-(3-chlorophenyl)-propyl]-2-ethyl-quinazoline-8-carboxylic acid amide, and pharmaceutically acceptable salts thereof.

5. A pharmaceutical composition comprising a compound according to any of claims 1 to 4, or a pharmaceutically acceptable salt thereof, as active ingredient, together with a pharmaceutically acceptable carrier.

6. A method for treating hyperproliferative diseases, comprising administering to a subject a compound of any of claims 1 to 4, or a pharmaceutically acceptable salt, thereof.

7. The method of claim 6, wherein the disease is selected from the group consisting of cancer, inflammation, pancreatitis or kidney disease, pain, benign hyperplasia of the skin, restenosis, prostate, diseases related to vasculogenesis or angiogenesis, tumor angiogenesis, skin diseases selected from psoriasis, eczema, and sclerodema, diabetes, diabetic retinopathy, retinopathy of prematurity, age-related macular degeneration, hemangioma, glioma, melanoma and Kaposi's sarcoma.

8. Set (kit) consisting of separate packs of
a) an effective amount of a compound according to one or more of claims 1 to 4 or a pharmaceutically acceptable salt and
b) an effective amount of a further medicament active ingredient.

9. Process for the manufacture of compounds of Formula (I),
wherein X is N and Y is NH, and all other substituents have the meaning as defined for Formula (I) in claim 1, wherein a carboxylic acid ester of Formula (IV)

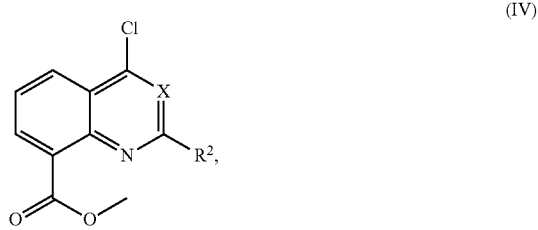

is reacted with a compound of Formula (III)

    (III), to yield a compound of Formula (II)

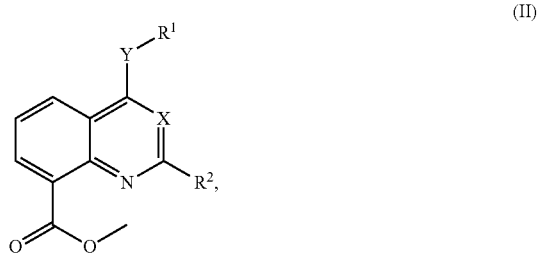

which is finally converted into the carboxylic amide of Formula (I)

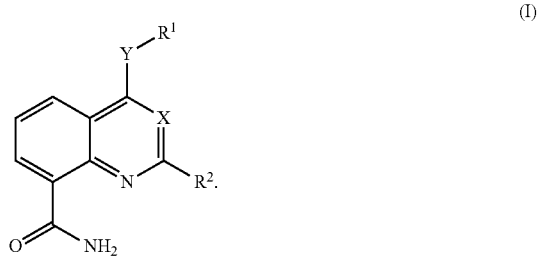

* * * * *